(12) United States Patent
Kanji et al.

(10) Patent No.: US 7,378,103 B2
(45) Date of Patent: May 27, 2008

(54) COSMETIC COMPOSITION COMPRISING A POLYGLYCEROLATED SILICONE ELASTOMER

(75) Inventors: Mohamed Kanji, Edison, NJ (US); Shao Xiang Lu, Plainsboro, NJ (US); Dhaval Patel, Edison, NJ (US)

(73) Assignee: L'Oreal, Paris (FR)

( * ) Notice: Subject to any disclaimer, the term of this patent is extended or adjusted under 35 U.S.C. 154(b) by 165 days.

(21) Appl. No.: 11/085,509

(22) Filed: Mar. 22, 2005

(65) Prior Publication Data
US 2005/0220728 A1    Oct. 6, 2005

Related U.S. Application Data

(60) Provisional application No. 60/554,929, filed on Mar. 22, 2004.

(51) Int. Cl.
*A61K 8/00* (2006.01)
(52) U.S. Cl. ......................... 424/401; 424/59
(58) Field of Classification Search ............... 424/401, 424/59; 514/63
See application file for complete search history.

(56) References Cited

U.S. PATENT DOCUMENTS

| | | | |
|---|---|---|---|
| 2,283,218 A | 5/1942 | McCullough | |
| 2,463,264 A | 3/1949 | Graenacher et al. | |
| 3,589,578 A | 6/1971 | Monforts | |
| 3,836,537 A | 9/1974 | Boerwinkle et al. | |
| 3,937,811 A | 2/1976 | Papantoniou et al. | |
| 4,031,307 A | 6/1977 | DeMartino et al. | |
| 4,131,576 A | 12/1978 | Iovine et al. | |
| 4,367,390 A | 1/1983 | Balleys et al. | |
| 4,693,935 A | 9/1987 | Mazurek | |
| 4,728,571 A | 3/1988 | Clemens et al. | |
| 4,887,622 A | 12/1989 | Gueret | |
| 4,972,037 A | 11/1990 | Garbe et al. | |
| 4,981,902 A | 1/1991 | Mitra et al. | |
| 4,981,903 A | 1/1991 | Garbe et al. | |
| 5,061,481 A | 10/1991 | Suzuki et al. | |
| 5,166,355 A | 11/1992 | Leistner et al. | |
| 5,208,360 A | 5/1993 | Ward et al. | |
| 5,209,924 A | 5/1993 | Garbe et al. | |
| 5,219,560 A | 6/1993 | Suzuki et al. | |
| 5,236,698 A | 8/1993 | Richard et al. | |
| 5,236,986 A | 8/1993 | Sakuta | |
| 5,237,071 A | 8/1993 | Leistner et al. | |
| 5,252,323 A | 10/1993 | Richard et al. | |
| 5,362,482 A | 11/1994 | Yoneyama et al. | |
| 5,412,004 A | 5/1995 | Tachibana et al. | |
| 5,468,477 A | 11/1995 | Kumar et al. | |
| 5,492,426 A | 2/1996 | Gueret | |
| 5,538,793 A | 7/1996 | Inokuchi et al. | |
| 5,585,091 A | 12/1996 | Pelzer et al. | |
| 5,599,533 A | 2/1997 | Stepniewski et al. | |
| 5,625,005 A | 4/1997 | Mallya et al. | |
| 5,725,882 A | 3/1998 | Kumar et al. | |
| 5,783,657 A | 7/1998 | Pavlin et al. | |
| 5,801,244 A | 9/1998 | Raspanti | |
| 5,811,487 A | 9/1998 | Schulz, Jr. et al. | |
| 5,837,793 A | 11/1998 | Harashima et al. | |
| 5,849,275 A | 12/1998 | Calello et al. | |
| 5,849,318 A | 12/1998 | Imai et al. | |
| 5,849,909 A | 12/1998 | Richard et al. | |
| 5,851,517 A | 12/1998 | Mougin et al. | |
| 5,948,393 A | 9/1999 | Tomomasa et al. | |
| 5,955,060 A | 9/1999 | Huglin et al. | |
| 6,033,650 A | 3/2000 | Calello et al. | |
| 6,059,473 A | 5/2000 | Gueret | |
| 6,093,385 A | 7/2000 | Habeck et al. | |
| 6,159,455 A | 12/2000 | Habeck et al. | |
| 6,238,649 B1 | 5/2001 | Habeck et al. | |
| 6,328,495 B1 | 12/2001 | Gueret | |
| 6,372,235 B1 | 4/2002 | Livoreil et al. | |

(Continued)

FOREIGN PATENT DOCUMENTS

DE    197 46 654    2/1999

(Continued)

OTHER PUBLICATIONS

Shin Etsu Chemical Co., Ltd, Product Brochure KSG Series, 1999, p. 1-12.*

(Continued)

*Primary Examiner*—Johann Richter
*Assistant Examiner*—Konata M George
(74) *Attorney, Agent, or Firm*—Francois Maniere; Maria Luisa Balasta; Steven Trzaska

(57) ABSTRACT

The invention relates to a cosmetic composition containing, in at least one cosmetically acceptable medium, at least one polyglycerolated silicone elastomer and at least one ingredient chosen from at least one emulsifying elastomer different from the polyglycerolated silicone elastomer, at least one film forming polymer, at least one water-soluble humectant, at least one coated pigment, at least one structuring agent, at least one photoprotective system capable of screening out UV radiation, at least one non-emulsifying spherical silicone elastomer, at least one fiber, at least one non-crosslinked surfactant, with the proviso that the non-crosslinked surfactant is not chosen from polyglycerolated non-crosslinked silicone surfactants, at least one hydrocarbyl-functional siloxane, at least one low molecular weight phenyl-substituted siloxane and at least one cosmetically-suitable active ingredient.

26 Claims, No Drawings

U.S. PATENT DOCUMENTS

| | | |
|---|---|---|
| 6,386,781 B1 | 5/2002 | Gueret |
| 6,387,355 B2 | 5/2002 | Heidenfelder et al. |
| 6,391,289 B2 | 5/2002 | Heidenfelder et al. |
| 6,403,106 B1 | 6/2002 | Sebag et al. |
| 6,436,373 B1 | 8/2002 | Habeck et al. |
| 6,484,731 B1 | 11/2002 | Lacout |
| 6,534,647 B1 | 3/2003 | Stevens et al. |
| 6,545,174 B2 | 4/2003 | Habeck et al. |
| 6,581,610 B1 | 6/2003 | Gueret |
| 6,843,611 B2 | 1/2005 | Blondeel et al. |
| 2002/0131947 A1 | 9/2002 | Nakanishi |
| 2002/0172696 A1 | 11/2002 | Ferrari |
| 2003/0012802 A1 | 1/2003 | Arnaud-Sebillotte et al. |
| 2003/0185771 A1 | 10/2003 | Kamei et al. |
| 2004/0241126 A1 | 12/2004 | Sakuta |
| 2005/0065046 A2 | 3/2005 | Jager Lezer |
| 2002/0098217 A1 | 7/2005 | Piot et al. |
| 2006/0034875 A1 | 2/2006 | Tetsuo et al. |

FOREIGN PATENT DOCUMENTS

| | | |
|---|---|---|
| DE | 197 55 649 | 6/1999 |
| DE | 198 55 649 | 6/2000 |
| EP | 0080976 | 6/1983 |
| EP | 0096459 | 12/1983 |
| EP | 0242219 | 10/1987 |
| EP | 0285886 | 10/1988 |
| EP | 0295886 | 12/1988 |
| EP | 0388582 | 9/1990 |
| EP | 0412704 | 2/1991 |
| EP | 0412707 | 2/1991 |
| EP | 0507691 | 10/1992 |
| EP | 0507692 | 10/1992 |
| EP | 0517104 | 12/1992 |
| EP | 0518772 | 12/1992 |
| EP | 0518773 | 12/1992 |
| EP | 0570838 | 11/1993 |
| EP | 0582152 | 2/1994 |
| EP | 0640105 | 3/1995 |
| EP | 0669323 | 8/1995 |
| EP | 0708114 | 4/1996 |
| EP | 0749747 | 12/1996 |
| EP | 0765656 | 4/1997 |
| EP | 0775698 | 5/1997 |
| EP | 0790243 | 8/1997 |
| EP | 0796851 | 9/1997 |
| EP | 0815836 | 1/1998 |
| EP | 0863145 | 9/1998 |
| EP | 0878469 | 11/1998 |
| EP | 0893119 | 1/1999 |
| EP | 0895467 | 2/1999 |
| EP | 0933376 | 8/1999 |
| EP | 0944624 | 9/1999 |
| EP | 0967200 | 12/1999 |
| EP | 1008586 | 6/2000 |
| EP | 1 068 854 | 1/2001 |
| EP | 1 086 945 | 3/2001 |
| EP | 1086197 | 3/2001 |
| EP | 1086683 | 3/2001 |
| EP | 1133980 | 9/2001 |
| EP | 1133981 | 9/2001 |
| EP | 1201221 | 5/2002 |
| EP | 1213316 | 6/2002 |
| EP | 1266647 | 12/2002 |
| EP | 1327668 | 7/2003 |
| EP | 1400234 | 3/2004 |
| EP | 1416016 | 5/2004 |
| EP | 1424373 | 6/2004 |
| EP | 1496080 | 1/2005 |
| EP | 1550687 | 7/2005 |
| FR | 2077143 | 10/1971 |
| FR | 2232303 | 1/1975 |
| FR | 2393573 | 1/1979 |
| FR | 2727609 | 6/1996 |
| FR | 2761959 | 10/1998 |
| FR | 2775566 | 9/1999 |
| FR | 2791042 | 9/2000 |
| FR | 2792618 | 10/2000 |
| FR | 2722380 | 1/2001 |
| FR | 2796529 | 1/2001 |
| FR | 2806273 | 9/2001 |
| FR | 2831430 | 5/2003 |
| FR | 2844710 | 3/2004 |
| FR | 2848422 | 6/2004 |
| FR | 2860143 | 4/2005 |
| FR | 2864894 | 7/2005 |
| GB | 1331819 | 9/1973 |
| GB | 2000026 | 1/1979 |
| GB | 2303549 | 2/1997 |
| JP | 61-194009 | 8/1986 |
| JP | 05-339125 | 12/1993 |
| JP | 2002038013 | 2/2002 |
| JP | 2002179798 | 6/2002 |
| JP | 2004346046 | 12/2004 |
| JP | 2005171146 | 6/2005 |
| JP | 2005200369 | 7/2005 |
| JP | 2005239645 | 9/2005 |
| JP | 2005263794 | 9/2005 |
| WO | WO 93/04665 | 3/1993 |
| WO | WO 93/23008 | 11/1993 |
| WO | WO 93/23009 | 11/1993 |
| WO | WO 93/23446 | 11/1993 |
| WO | WO 95/00578 | 1/1995 |
| WO | WO 95/03776 | 2/1995 |
| WO | WO 95/06078 | 3/1995 |
| WO | WO 01/03538 | 1/2001 |
| WO | WO 02/47031 | 6/2002 |
| WO | WO 02/47619 | 6/2002 |
| WO | WO 02/056847 | 7/2002 |
| WO | WO02056854 | 7/2002 |
| WO | WO 03/018423 | 3/2003 |
| WO | WO 03075864 | 9/2003 |
| WO | WO 03/105788 | 12/2003 |
| WO | WO 2004024798 | 3/2004 |
| WO | WO 94/028487 | 4/2004 |
| WO | WO 94/055078 | 7/2004 |
| WO | WO 2005/067869 | 7/2005 |

OTHER PUBLICATIONS

Shin-Etsu Chemical Co. Ltd, Shin-Etsu Silicones for Personal Care, Cosmetic Application Lab, Feb. 2004.*

"Specialist Surfactants" edited by D. Robb, 1997, pp. 209-263, Chapter 8 by P. Terech.

"Solubility Parameter Values" by Eric A. Grulke in the book "Polymer Handbook", 3rd Edition, Chapter VII, p. 519-559.

Article by C. M. Hansen: "The Three-Dimensional Solubility Parameters", J. Paint Technol. 39, 105 (1967).

Article by Gillman K.F., Polymer Letters, vol. 5, p. 477-481 (1967).

Shin-Etsu Chemical Co., Ltd., Shin-Etsu Silicones for Personal Care, Cosmetic Application Lab, Feb. 2004.

* cited by examiner

COSMETIC COMPOSITION COMPRISING A POLYGLYCEROLATED SILICONE ELASTOMER

This application is a non-provisional application of and claims benefit to U.S. Provisional Application No. 60/554,929, filed Mar. 22, 2004 which is incorporated by reference in its entirety for all purposes.

BACKGROUND OF THE INVENTION

Cosmetic compositions comprising silicone oils are becoming quite popular because of their feel and spreadability characteristics. However, the incorporation of silicone oils, be they volatile or non volatile, is difficult. Often, such compositions tend to be unstable. Attempts have been made to use alkoxylated silicone emulsifiers in cosmetic compositions as exemplified in U.S. Pat. No. 5,362,482 for the purpose of stabilizing silicone emulsions, or crosslinked siloxane elastomers such as in U.S. Pat. No. 5,599,533. Silicone emulsions provide improved cosmetic compositions with cushiony, soft and silky feel upon application. Traditionally, water in oil emulsions with high level of dispersed phase do not provide a good feel during application and their stability is questionable. Creams too often are heavy and feel greasy.

SUMMARY OF THE INVENTION

The present invention relates to a cosmetic composition comprising a polyglycerolated silicone elastomer for application onto keratinous materials such as the skin, the lips, the eyelashes, the eyebrows the nails or the hair. The composition is more particularly intended to be applied to the skin or the lips.

The composition according to the invention may be a makeup composition or a care composition for keratinous materials, in particular for the skin and the lips.

The makeup composition may be a lip makeup product (lipstick, lip gloss), a foundation, an eyeshadow, a makeup rouge, a concealer product, an eyeliner, a body makeup product, a mascara, a nail varnish or a hair makeup product.

The care composition may be a care product for body and facial skin, especially an antisun product or a skin-coloring product (such as a self-tanning product). The composition may also be a haircare product, especially for holding the hairstyle or for shaping the hair.

The aim of the present invention is that of providing novel routes for formulating cosmetic products.

The present invention is thus directed to a composition comprising:
  a) at least one cosmetically acceptable medium;
  b) at least one polyglycerolated silicone elastomer;
  c) at least one ingredient chosen from at least one emulsifying elastomer different from the polyglycerolated silicone elastomer, at least one film forming polymer, at least one water-soluble humectant, at least one coated pigment, at least one structuring agent, at least one photoprotective system capable of screening out UV radiation, at least one non-emulsifying spherical silicone elastomer, at least one fiber, at least one non-crosslinked surfactant, with the proviso that the non-crosslinked surfactant is not chosen from polyglycerolated non-crosslinked silicone surfactants, at least one hydrocarbyl-functional siloxane, at least one low molecular weight phenyl-substituted siloxane and at least one cosmetically-suitable active ingredient.

The present invention is also directed to a process for treating a keratinous material involving contacting the keratinous material with the above-disclosed composition.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

The term "cosmetically acceptable medium" means a medium that is compatible with human keratinous materials.

Polyglycerolated Silicone Elastomer:

The polyglycerolated silicone elastomer present in the composition according to the invention is a crosslinked elastomeric organopolysiloxane that may be obtained by a crosslinking addition reaction of diorganopolysiloxane containing at least one hydrogen atom linked to silicon and of polyglycerolated compounds containing ethylenically unsaturated groups, especially in the presence of a platinum catalyst.

Preferably, the crosslinked elastomeric organopolysiloxane is obtained by a crosslinking addition reaction (A) of diorganopolysiloxane containing at least two hydrogens each linked to a silicon, and (B) of glycerolated compounds containing at least two ethylenically unsaturated groups, especially in the presence (C) of a platinum catalyst.

In particular, the organopolysiloxane may be obtained by reaction of a polyglycerolated compound containing dimethylvinylsiloxy end groups and of methylhydrogenopolysiloxane containing trimethylsiloxy end groups, in the presence of a platinum catalyst.

Compound (A) is the base reagent for the formation of elastomeric organopolysiloxane and the crosslinking is performed by an addition reaction of compound (A) with compound (B) in the presence of the catalyst (C).

Compound (A) is in particular an organopolysiloxane containing at least 2 hydrogen atoms linked to different silicon atoms in each molecule.

Compound (A) may have any molecular structure, in particular a linear chain or branched chain structure or a cyclic structure.

Compound (A) may have a viscosity at 25° C. ranging from 1 to 50,000 centistokes, especially in order to have good miscibility with compound (B).

The organic groups linked to silicon atoms of the compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. The said organic group is preferably chosen from methyl, phenyl and lauryl groups.

Compound (A) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, or dimethylsiloxane-methylhydrogenosiloxane-laurylmethylsiloxane copolymers containing trimethylsiloxy end groups.

Compound (B) may be a polyglycerolated compound corresponding to formula (B') below:

$$C_mH_{2m-1}-O-[Gly]n-C_mH_{2m-1} \qquad (B')$$

in which m is an integer ranging from 2 to 6, n is an integer ranging from 2 to 200, preferably ranging from 2 to 100, preferably ranging from 2 to 50, preferably n ranging from 2 to 20, preferably ranging from 2 to 10 and preferably ranging from 2 to 5, and in particular equal to 3; Gly denotes:

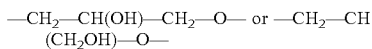

—CH$_2$—CH(OH)—CH$_2$—O— or —CH$_2$—CH(CH$_2$OH)—O—

Advantageously, the sum of the number of ethylenic groups per molecule of compound (B) and of the number of hydrogen atoms linked to silicon atoms per molecule of compound (A) is at least 4.

It is advantageous for compound (A) to be added in an amount such that the molar ratio between the total amount of hydrogen atoms linked to silicon atoms in compound (A) and the total amount of all the ethylenically unsaturated groups in compound (B) is within the range from 1/1 to 20/1.

Compound (C) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in from 0.1 to 1,000 parts by weight, better still from 1 to 100 parts by weight, as clean platinum metal per 1,000 parts by weight of the total amount of compounds (A) and (B).

The polyglycerolated silicone elastomer may be conveyed in gel form in at least one hydrocarbon-based oil and/or one silicone oil. In these gels, the polyglycerolated elastomer is often in the form of non-spherical particles.

Polyglycerolated silicone elastomers that may be used include those sold under the names "KSG-710", "KSG-810", "KSG-820", "KSG-830" and "KSG-840" by the company Shin-Etsu.

The polyglycerolated silicone elastomer may be present in the composition of the present invention in an amount of from 0.1% to 50% by weight, preferably from 0.1% to 40% by weight, preferably from 0.5% to 30% by weight, more preferably from 0.5% to 20% by weight and even more preferably from 1% to 10% by weight based on the weight of the composition.

Additional Emulsifying Silicone Elastomer:

The composition according to the invention may comprise an additional emulsifying silicone elastomer different from the polyglycerolated silicone elastomer described above.

The term "emulsifying silicone elastomer" means a silicone elastomer comprising at least one hydrophilic chain other than a polyglycerolated chain as described above.

In particular, the additional emulsifying silicone elastomer may be chosen from polyoxyalkylenated silicone elastomers.

The polyoxyalkylenated silicone elastomer is a crosslinked organopolysiloxane that may be obtained by a crosslinking addition reaction of diorganopolysiloxane containing at least one hydrogen linked to silicon and of a polyoxyalkylene containing at least two ethylenically unsaturated groups.

Preferably, the polyoxyalkylenated crosslinked organopolysiloxane is obtained by a crosslinking addition reaction (A1) of diorganopolysiloxane containing at least two hydrogens each linked to a silicon, and (B1) of polyoxyalkylene containing at least two ethylenically unsaturated groups, especially in the presence (C1) of a platinum catalyst, as described, for example, in patents U.S. Pat. No. 5,236,986 and U.S. Pat. No. 5,412,004.

In particular, the organopolysiloxane may be obtained by reaction of polyoxyalkylene (especially polyoxyethylene and/or polyoxypropylene) containing dimethylvinylsiloxy end groups and of methylhydrogenopolysiloxane containing trimethylsiloxy end groups, in the presence of a platinum catalyst.

The organic groups linked to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, dimethylsiloxane-methylhydrogenosiloxane-laurylmethylsiloxane copolymers containing trimethylsiloxy end groups.

Compound (C1) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, in particular polyoxyalkylenes containing at least two vinyl groups, reacting with Si—H bonds of a polysiloxane.

The polyoxyalkylenated silicone elastomers may be conveyed in the form of a gel consisting of an elastomeric organopolysiloxane included in at least one hydrocarbon-based oil and/or one silicone oil. In these gels, the organopolysiloxane particles are often non-spherical particles.

Polyoxyalkylenated elastomers are especially described in patents U.S. Pat. No. 5,236,986, U.S. Pat. No. 5,412,004, U.S. Pat. No. 5,837,793 and U.S. Pat. No. 5,811,487, the entire contents of which are incorporated herein by reference.

Polyoxyalkylenated silicone elastomers that may be used include those sold under the names "KSG-21", "KSG-20", "KSG-30", "KSG-31", "KSG-32", "KSG-33", "KSG-210", "KSG-310", "KSG-320", "KSG-330", "KSG-340" and "X-226146" by the company Shin-Etsu, or "DC9010" and "DC9011" by the company Dow Corning.

The additional emulsifying silicone elastomer may be present in the composition in an amount of from 0.1% to 50% by weight, preferably from 0.1% to 40% by weight, preferably from 0.5% to 30% by weight, more preferably from 0.5% to 20% by weight and even more preferably from 1% to 10% by weight based on the weight of the composition.

Non-emulsifying Spherical Silicone Elastomer:

The composition according to the invention may comprise a non-emulsifying spherical silicone elastomer.

The term "non-emulsifying" defines elastomers not containing a hydrophilic chain, such as polyoxyalkylene or polyglycerolated units.

The non-emulsifying spherical silicone elastomer is an elastomeric crosslinked organopolysiloxane that may be obtained by a crosslinking addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking coupling reaction between a diorganopolysiloxane containing hydroxyl end groups and a diorganopolysiloxane containing at least one hydrogen linked to silicon, especially in the presence of an organotin compound; or by a crosslinking coupling reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the elastomeric crosslinked organopolysiloxane is obtained by a crosslinking addition reaction (A2) of diorganopolysiloxane containing at least two hydrogens each linked to a silicon, and (B2) of diorganopolysiloxane containing at least two ethylenically unsaturated groups linked to silicon, especially in the presence (C2) of a platinum catalyst, as described, for example, in patent application EP0295886A.

In particular, the organopolysiloxane may be obtained by reaction of dimethylpolysiloxane containing dimethylvinylsiloxy end groups and of methylhydrogenopolysiloxane containing trimethylsiloxy end groups, in the presence of a platinum catalyst.

Compound (A2) is the base reagent for the formation of elastomeric organopolysiloxane, and the crosslinking is performed by an addition reaction of compound (A2) with compound (B2) in the presence of a catalyst (C2).

Compound (A2) is advantageously a diorganopolysiloxane containing at least two lower (for example C2-C4) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (A2) may have a branched-chain, linear-chain, cyclic or network structure, but the linear-chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

Compound (B2) is in particular an organopolysiloxane containing at least 2 hydrogens linked to silicon in each molecule and is thus the crosslinking agent for the compound (A2).

Advantageously, the sum of the number of ethylenic groups per molecule of compound (A2) and the number of hydrogen atoms linked to silicon per molecule of compound (B2) is at least 4.

Compound (B2) may be in any molecular structure, especially of linear-chain or branched-chain structure, or cyclic structure.

Compound (B2) may have a viscosity at 25° C. ranging from 1 to 50,000 centistokes, especially in order to have good miscibility with compound (A).

It is advantageous for compound (B2) to be added in an amount such that the molar ratio between the total amount of hydrogen atoms linked to silicon in compound (B2) and the total amount of all of the ethylenically unsaturated groups in compound (A2) is within the range from 1/1 to 20/1.

Compound (B2) may be chosen from methylhydrogenopolysiloxanes containing trimethylsiloxy end groups, dimethylsiloxane-methylhydrogenosiloxane copolymers containing trimethylsiloxy end groups, and dimethylsiloxane-methylhydrogenosiloxane cyclic copolymers.

Compound (C2) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in from 0.1 to 1,000 parts by weight, better still from 1 to 100 parts by weight, as clean platinum metal per 1,000 parts by weight of the total amount of compounds (A2) and (B2).

Other organic groups may be linked to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The elastomeric crosslinked organopolysiloxane particles may be conveyed in the form of a gel consisting of an elastomeric organopolysiloxane included in at least one hydrocarbon-based oil and/or one silicone oil. In these gels, the organopolysiloxane particles are often non-spherical particles. The elastomeric crosslinked organopolysiloxane particles may also be in powder form, especially in the form of spherical powder.

Non-emulsifying spherical silicone elastomers are especially described in patent applications JP61-194009 A, EP0242219 A, EP0285886 A and EP0765656 A, the entire contents of which are herein incorporated by reference.

Non-emulsifying spherical silicone elastomers that may be used include those sold under the names "DC 9040", "DC 9041", "DC 9509", "DC 9505" and "DC 9506" by the company Dow Corning.

The non-emulsifying spherical silicone elastomer may also be in the form of elastomeric crosslinked organopolysiloxane powder coated with silicone resin, especially with silsesquioxane resin, as described, for example, in patent U.S. Pat. No. 5,538,793, the entire content of which is herein incorporated by reference. Such elastomers are sold under the names "KSP-100", "KSP-101", "KSP-102", "KSP-103", "KSP-104" and "KSP-105" by the company Shin-Etsu.

Other elastomeric crosslinked organopolysiloxanes in the form of spherical powders may be hybrid silicone powders functionalized with fluoroalkyl groups, sold especially under the name "KSP-200" by the company Shin-Etsu; hybrid silicone powders functionalized with phenyl groups, sold especially under the name "KSP-300" by the company Shin-Etsu.

The non-emulsifying spherical silicone elastomer may be present in the composition in an amount of from 0.1% to 95% by weight, preferably from 0.5% to 75% by weight and preferably from 1% to 50% by weight, more preferably from 1% to 40% by weight and more preferably from 1% to 30% by weight, based on the weight of the composition.

Moisturizer:

The composition according to the invention may comprise a moisturizer, in particular a moisturizer that is miscible with water at 25° C.

The moisturizer may especially be a polyhydric alcohol chosen in particular from polyols especially containing from 2 to 20 carbon atoms, preferably containing from 2 to 10 carbon atoms and preferably containing from 2 to 6 carbon atoms. The moisturizer may be chosen, for example, from glycerol, propylene glycol, butylene glycol, pentylene glycol, hexylene glycol, dipropylene glycol, diethylene glycol, sorbitol, hydroxypropyl sorbitol and 1,2,6-hexanetriol; glycol ethers (especially containing from 3 to 16 carbon atoms) such as mono-, di- or tripropylene glycol C1-C4)alkyl ethers and mono-, di- or triethylene glycol (C1-C4)alkyl ethers; and mixtures thereof.

The moisturizer may be present in the composition of the present invention in an amount of from 1% to 60% by weight, preferably from 2% to 40% by weight and preferably from 3% to 20% by weight, based on the weight of the composition.

Film-forming Polymers:

The term "film-forming polymer", in general, means a polymer capable of forming, by itself or in the presence of an auxiliary film-forming agent, a continuous film that adheres to a support, especially to keratin materials, and preferably a cohesive film, and better still a film whose cohesion and mechanical properties are such that the said film may be isolated from the said support.

In one embodiment, the film-forming organic polymer is at least one polymer chosen from the group comprising:

film-forming polymers that are soluble in an organic liquid medium, in particular liposoluble polymers, when the organic liquid medium comprises at least one oil;

film-forming polymers that are dispersible in an organic solvent medium, in particular polymers in the form of non-aqueous dispersions of polymer particles, preferably dispersions in silicone oils or in hydrocarbon-based oils; in one embodiment, the non-aqueous polymer dispersions comprise polymer particles stabilized at their surface with at least one stabilizer;

film-forming polymers in the form of aqueous dispersions of polymer particles, often known as "lattices"; in this case, the composition comprises an aqueous phase;

water-soluble film-forming polymers; in this case, the composition comprises an aqueous phase.

Among the film-forming polymers that may be used in the composition of the present invention, mention may be made of synthetic polymers, of free-radical type or of polycondensate type; polymers of natural origin, and mixtures thereof. Film-forming polymers that may be mentioned in particular include acrylic polymers, polyurethanes, polyesters, polyamides, polyureas, cellulose-based polymers, for instance nitrocellulose, silicone polymers, in particular silicone resins and silicone-grafted acrylic polymers.

Film-forming polymers are especially described in the international patent application filed under the number PCT/FR03/02849, the entire content of which is hereby incorporated by reference. They may be organic or inorganic polymers.

Suitable film-forming organic polymers may be chosen from:

film-forming polymers which are soluble in the organic liquid medium, in particular fat-soluble polymers, when the organic liquid medium comprises at least one oil, film-forming polymers which are dispersible in the organic liquid solvent medium, in particular polymers in the form of non-aqueous dispersions of polymer particles, preferably dispersions in silicone oils or hydrocarbon-based oils; in one embodiment, the non-aqueous dispersions of polymer comprise polymer particles stabilized on their surface with at least one stabilizer, and are often referred to as "NADs" [non-aqueous dispersions], aqueous dispersions of particles of film-forming polymers, which are often known as "lattices"; in this case, the composition should comprise an aqueous phase besides the organic liquid medium, water-soluble film-forming polymers; in this case, the composition should comprise an aqueous phase besides the organic liquid medium.

In one embodiment, the film former is a film-forming organic polymer which is soluble in an organic liquid medium.

Polymers that are Soluble in an Organic Liquid Medium:

When the organic liquid medium of the composition comprises at least one oil, the film former may be a polymer that is soluble in the said oil. In this case, it is referred to as a fat-soluble polymer. The fat-soluble polymer may be of any chemical type and may especially be selected from:

a) fat-soluble, amorphous homopolymers and copolymers of olefins, of cycloolefins, of butadiene, of isoprene, of styrene, of vinyl ethers, esters or amides, or of (meth) acrylic acid esters or amides comprising a linear, branched or cyclic $C_4$-$C_{50}$ alkyl group, which are preferably amorphous. The preferred fat-soluble homopolymers and copolymers are obtained from monomers selected from the group consisting of isooctyl(meth)acrylate, isononyl(meth)acrylate, 2-ethylhexyl(meth)acrylate, lauryl(meth)acrylate, isopentyl (meth)acrylate, n-butyl(meth)acrylate, isobutyl(meth) acrylate, methyl(meth)acrylate, tert-butyl(meth) acrylate, tridecyl(meth)acrylate and stearyl(meth) acrylate, or mixtures thereof. Examples that will be mentioned include the alkyl acrylate/cycloalkyl acrylate copolymer sold by Phoenix Chem. under the name Giovarez AC-5099 ML, and vinylpyrrolidone copolymers, such as copolymers of a $C_2$ to $C_{30}$ alkene, such as a $C_3$ to $C_{22}$ alkene, and combinations thereof, may be used. As examples of VP copolymers that may be used in the invention, mention may be made of copolymers of VP/vinyl laurate, VP/vinyl stearate, butylated polyvinylpyrrolidone (PVP), VP/hexadecene, VP/triacontene or VP/acrylic acid/lauryl methacrylate. Particular fat-soluble copolymers that may be mentioned include:

i) silicone-acrylic graft polymers having a silicone skeleton and acrylic grafts or having an acrylic skeleton and silicone grafts, such as the product sold under the name SA 70.5 by 3M and described in patents U.S. Pat. No.

5,725,882, U.S. Pat. No. 5,209,924, U.S. Pat. No. 4,972,037, U.S. Pat. No. 4,981,903, U.S. Pat. No. 4,981,902 and U.S. Pat. No. 5,468,477, and in patents U.S. Pat. No. 5,219,560 and EP 0388582, the entire contents of which are hereby incorporated by reference;

ii) fat-soluble polymers belonging to one of the classes described above and bearing fluoro groups, in particular those described in patent U.S. Pat. No. 5,948,393 and the alkyl(meth)acrylate/perfluoroalkyl(meth)acrylate copolymers described in patents EP 0815836 and U.S. Pat. No. 5,849,318, the entire contents of which are hereby incorporated by reference;

iii) polymers or copolymers resulting from the polymerization or copolymerization of an ethylenic monomer comprising one or more ethylenic, preferably conjugated, bonds (or dienes). As polymers or copolymers resulting from the polymerization or copolymerization of an ethylenic monomer, it is possible to use vinyl, acrylic or methacrylic copolymers.

In one embodiment, the film former is a block copolymer comprising at least one block composed of styrene units or styrene derivatives (for example methylstyrene, chlorostyrene or chloromethyl-styrene). The copolymer comprising at least one styrene block may be a diblock or triblock copolymer, or even a multiblock copolymer, in starburst or radial form. The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, a methacrylate (MA) block or a combination of these blocks. The copolymer comprising at least one block composed of styrene units or styrene derivatives may be a triblock copolymer, and in particular of the polystyrene/polyisoprene or polystyrene/polybutadiene type, such as those sold or manufactured under the name "Luvitol HSB" by BASF, and those of the polystyrene/-copoly(ethylene-propylene) type or alternatively of the polystyrene/copoly(ethylene-butylene) type, such as those sold or manufactured under the brand name "Kraton" by Shell Chemical Co. or Gelled Permethyl 99A by Penreco may be used. Styrene-methacrylate copolymers may also be used.

Copolymer comprising at least one block composed of styrene or styrene-derived units may be, for example, Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58 (blend of triblock polymer and of starburst block polymer), Gelled Permethyl 99A-753-59 (blend of triblock polymer and of starburst block polymer), Versagel 5970 and Versagel 5960 from Penreco (blend of triblock polymer and of starburst polymer in isododecane), and OS 129880, OS 129881 and OS 84383 from Lubrizol (styrene-methacrylate copolymer).

In one embodiment, the film former is selected from copolymers of a vinyl ester (the vinyl group being directly attached to the oxygen atom of the ester group and the vinyl ester having a saturated, linear or branched hydrocarbon-based radical of 1 to 19 carbon atoms, linked to the carbonyl of the ester group) and of at least one other monomer, which may be a vinyl ester (other than the vinyl ester already present), an α-olefin (containing from 8 to 28 carbon atoms), an alkyl vinyl ether (the alkyl group of which contains from 2 to 18 carbon atoms) or an allylic or methallylic ester (containing a saturated, linear or branched hydrocarbon-based radical of 1 to 19 carbon atoms, linked to the carbonyl of the ester group).

These copolymers may be partially crosslinked using crosslinking agents, which may be either of the vinyl type or of the allylic or methallylic type, such as tetraallyloxyethane, divinylbenzene, divinyl octanedioate, divinyl dodecanedioate, and divinyl octadecanedioate.

Examples of these copolymers that may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-di-methylpentanoate/vinyl laurate, vinyl dimethyl-propionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinyl-benzene, vinyl acetate/1-octadecene, crosslinked with 0.2% divinylbenzene, and allyl propionate/allyl stearate, crosslinked with 0.2% divinylbenzene.

Fat-soluble film-forming polymers that may also be mentioned include fat-soluble copolymers, and in particular those resulting from the copolymerization of vinyl esters containing from 9 to 22 carbon atoms or of alkyl acrylates or methacrylates, the alkyl radicals containing from 10 to 20 carbon atoms.

Such fat-soluble copolymers may be selected from copolymers of polyvinyl stearate, polyvinyl stearate crosslinked with divinylbenzene, with diallyl ether or with diallyl phthalate, polystearyl(meth)acrylate, polyvinyl laurate and polylauryl(meth)acrylate copolymers, these poly (meth)acrylates possibly being crosslinked with ethylene glycol dimethacrylate or tetraethylene glycol dimethacrylate.

The fat-soluble copolymers defined above are known and described especially in patent application FR-A-2232303, the entire content of which is hereby incorporated by reference; they may have a weight-average molecular weight ranging from 2,000 to 500,000 and preferably from 4,000 to 200,000.

As examples of fat-soluble polymers that may be used in the invention, mention may be made of polyalkylenes and $C_2$-$C_{20}$ alkene copolymers, in particular polybutene.

b) amorphous and fat-soluble polycondensates, preferably not comprising any groups donating hydrogen interactions, in particular aliphatic polyesters having $C_{4-50}$ alkyl side chains or else polyesters resulting from the condensation of fatty acid dimers, or even polyesters comprising a silicone-based segment in the form of a block, graft or end group, which are solid at ambient temperature, as defined in patent application FR 0113920, not yet published.

c) amorphous and fat-soluble polysaccharides comprising alkyl (ether or ester) side chains, in particular alkylcelluloses containing a saturated or unsaturated, linear or branched $C_1$ to $C_8$ alkyl radical, such as ethylcellulose and propylcellulose.

The film-forming polymer may be selected in particular from cellulose-based polymers such as nitro-cellulose, cellulose acetate, cellulose acetobutyrate, cellulose acetopropionate or ethylcellulose, or else from polyurethanes, acrylic polymers, vinyl polymers, polyvinyl butyrals, alkyd resins, resins derived from aldehyde condensation products, such as arylsulphonamide-formaldehyde resins, for instance toluenesulphonamide-formaldehyde resin, and arylsulphonamide epoxy resins.

Film-forming polymers that may especially be used include nitrocellulose RS ⅛ sec.; RS ¼ sec.; ½ sec.; RS 5 sec.; RS 15 sec.; RS 35 sec.; RS 75 sec.; RS 150 sec.; AS ¼ sec.; AS ½ sec.; SS ¼ sec.; SS ½ sec.; SS 5 sec., sold especially by the company Hercules; the toluenesulphonamide-formaldehyde resins "Ketjentflex MS80" from the company Akzo or "Santolite MHP" and "Santolite MS80" from the company Faconnier or "Resimpol 80" from the company Pan Americana, the alkyd resin "Beckosol Ode 230-70-E" from the company Dainippon, the acrylic resin "Acryloid B66" from the company Rohm & Haas, and the polyurethane resin "Trixene PR 4127" from the company Baxenden.

d) silicone resins which are soluble or swellable by silicone oils. These resins are partially crosslinked polyorganosiloxanes which, depending on the degree of crosslinking, will be soluble or swellable by the silicone oils of the oily phase of the organic liquid medium. These silicone resins may be selected from the following non-limitative list: MQ resins or trimethylsiloxysilicates, polysilsesquioxanes or crosslinked dimethicone/vinyldimethicone polymers.

Non-aqueous Dispersions of Polymer Particles:

The composition may contain a film former selected from non-aqueous dispersions of polymer particles. The particles are generally spherical. Before being incorporated into the composition of the invention, the particles are generally dispersed in a physiologically acceptable liquid fatty phase, such as hydrocarbon-based oils or silicone oils. According to one mode of implementation, these dispersions are generally known as NADs (non-aqueous dispersions) of polymer, as opposed to networks, which are aqueous dispersions of polymer. These dispersions may especially be in the form of nanoparticles of polymers in stable dispersion in the said fatty phase. In one embodiment the nanoparticles are between 5 nm and 600 nm in size. However, it is possible to obtain polymer particles ranging up to 1 µm in size.

One of the advantages of the polymer dispersion of the composition of the invention is the possibility of varying the glass transition temperature ($T_g$) of the polymer or the polymer system (polymer plus additive of the plasticizer type), and of thus going from a hard polymer to a more or less soft polymer, making it possible to adjust the mechanical properties of the composition depending on the intended application and in particular on the film deposited.

The polymers in dispersion which may be used in the composition of the invention preferably have a molecular weight ranging from about 2,000 to 10,000,000 and a $T_g$ ranging from −100° C. to 300° C. and better still from −50° C. to 50° C. and preferably from −10° C. to 100° C.

It is possible to use film-forming polymers, that preferably have a low $T_g$, of less than or equal to the temperature of the skin and especially less than or equal to 40° C. A dispersion is thus obtained which can form a film when it is applied to a support.

Among the film-forming polymers which may be mentioned are free-radical, acrylic or vinyl homo-polymers or copolymers, preferably having a $T_g$ of less than or equal to 40° C. and especially ranging from −10° C. to 30° C., used alone or as a mixture.

The expression "free-radical polymer" means a polymer obtained by polymerization of monomers containing unsaturation, especially ethylenic unsaturation, each monomer being capable of homo-polymerizing (unlike polycondensates). The free-radical polymers may especially be vinyl polymers or copolymers, especially acrylic polymers.

The vinyl polymers may result from the polymerization of ethylenically unsaturated monomers containing at least one acid group and/or esters of these acidic monomers and/or amides of these acids.

As monomers bearing an acidic group, it is possible to use α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously selected from the esters of (meth)acrylic acid (also known as (meth)acrylates), for instance alkyl(meth)acrylates, in particular of a $C_1$-$C_{20}$ and preferably a $C_1$-$C_6$ alkyl, aryl(meth) acrylates, in particular of a $C_6$-$C_{10}$ aryl, and hydroxyalkyl (meth)acrylates, in particular of a $C_2$-$C_6$ hydroxyalkyl. Alkyl (meth)acrylates which may be mentioned include methyl, ethyl, butyl, isobutyl, 2-ethylhexyl and lauryl(meth)acrylate. Hydroxyalkyl(meth)acrylates which may be mentioned include hydroxyethyl(meth)acrylate and 2-hydroxypropyl (meth)acrylate. Aryl(meth)acrylates which may be mentioned include benzyl or phenyl acrylate.

The (meth)acrylic acid esters that are particularly preferred are alkyl(meth)acrylates.

The free-radical polymers that are preferably used are copolymers of (meth)acrylic acid and of an alkyl(meth) acrylate, especially of a $C_1$-$C_4$ alkyl. More preferably, methyl acrylates may be used, optionally copolymerized with acrylic acid.

The amides of the acidic monomers which may be mentioned include (meth)acrylamides, and especially N-alkyl (meth)acrylamides, in particular of a $C_2$-$C_{12}$ alkyl, such as N-ethylacrylamide, N-t-butylacrylamide and N-octylacrylamide; N-di($C_1$-$C_4$)alkyl(meth)acryl-amides.

The vinyl film-forming polymers can result from the polymerization of monomers containing ethylenic unsaturation and containing at least one acidic group and/or esters of these acidic monomers and/or amides of these acidic monomers.

Monomers bearing an acidic group which may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously selected from (meth)acrylic acid esters (also known as (meth)acrylates), especially (meth)acrylates of an alkyl, in particular of a $C_1$-$C_{30}$ and preferably a $C_1$-$C_{20}$ alkyl, (meth) acrylates of an aryl, in particular of a $C_6$-$C_{10}$ aryl, and (meth)acrylates of a hydroxyalkyl, in particular of a $C_2$-$C_6$ hydroxyalkyl.

Among the alkyl(meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates that may be mentioned are hydroxyethyl acrylate, 2-hydroxy-propyl acrylate, hydroxyethyl methacrylate and 2-hydroxypropyl methacrylate.

Among the aryl(meth)acrylates that may be mentioned are benzyl acrylate and phenyl acrylate.

The (meth)acrylic acid esters that are particularly preferred are the alkyl(meth)acrylates.

According to the present invention, the alkyl group of the esters may be either fluorinated or perfluorinated, i.e. some or all of the hydrogen atoms of the alkyl group are substituted by fluorine atoms.

Examples of amides of the acidic monomers that may be mentioned are (meth)acrylamides, and especially N-alkyl (meth)acrylamides, in particular of a $C_2$-$C_{12}$ alkyl. Among the N-alkyl(meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of monomers selected from vinyl esters and styrenic monomers. In particular, these monomers may be polymerized with acidic monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrenic monomers that may be mentioned are styrene and alpha-methylstyrene.

Examples of suitable fat-soluble or dispersible polymers or copolymers which may be employed in the present invention include, but are not limited to, polyurethanes, polyurethane-acrylics, polyureas, polyurea-polyurethanes, polyester-polyurethanes, polyether-polyurethanes, polyesters, polyesteramides, fatty-chain polyesters, alkyds; acrylic and/or vinyl polymers or copolymers; acrylic-silicone copolymers; polyacrylamides; silicone polymers, for example silicone polyurethanes or silicone acrylics, and fluoro polymers, and mixtures thereof.

The polymer(s) in oily dispersion may represent (as solids or active substance) from 0.1 to 60%, preferably from 2 to 40%, and more preferably from 4 to 25% by weight of the composition. For a stabilizer that is solid at ambient temperature, the amount of solids in the dispersion represents the total amount of polymer and stabilizer.

The fat-soluble or dispersible polymers may be used in an amount ranging from 0.01% to 20% by weight, preferably from 0.1% to 10% by weight, and more preferably from 1 to 10% by weight, based on the weight of the composition.

Aqueous Dispersions of Polymer Particles:

According to another embodiment, the film-forming polymer may be selected from aqueous dispersions of polymer particles, in the case where the composition according to the invention comprises an aqueous phase.

The aqueous dispersion comprising one or more film-forming polymers may be prepared by a person skilled in the art on the basis of his or her general knowledge, especially by emulsion polymerization or by dispersion of the preformed polymer.

Among the film-forming polymers which may be used in the composition according to the present invention, mention may be made of synthetic polymers, of polycondensate type or of free-radical type, polymers of natural origin, and mixtures thereof.

Among the polycondensates, mention may thus be made of anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes, and mixtures thereof.

The polyurethanes may be, for example, an aliphatic, cycloaliphatic or aromatic polyurethane, polyurea/polyurethane or polyurea copolymer, containing, alone or as a mixture, at least one block of linear or branched aliphatic and/or cycloaliphatic and/or aromatic polyester origin, and/or at least one block of aliphatic and/or cycloaliphatic and/or aromatic polyether origin, and/or at least one substituted or unsubstituted, branched or unbranched silicone block, for example polydimethylsiloxane or polymethylphenylsiloxane, and/or at least one block comprising fluoro groups.

The polyurethanes as defined in the invention may also be obtained from branched or unbranched polyesters or from alkyds containing mobile hydrogens, which are modified by means of a polyaddition with a diisocyanate and a difunctional organic co-reactive compound (for example dihydro, diamino or hydroxyamino), also containing either a carboxylic acid or carboxylate group, or a sulphonic acid or sulphonate group, or alternatively a neutralizable tertiary amine group or a quaternary ammonium group.

Mention may also be made of polyesters, polyesteramides, fatty-chain polyesters, polyamides and epoxy ester resins.

The polyesters may be obtained, in a known manner, by polycondensation of aliphatic or aromatic diacids with aliphatic or aromatic diols or with polyols. Succinic acid, glutaric acid, adipic acid, pimelic acid, suberic acid or sebacic acid may be used as aliphatic diacids. Terephthalic acid or isophthalic acid, or alternatively a derivative such as phthalic anhydride, may be used as aromatic diacids. Ethylene glycol, propylene glycol, diethylene glycol, neopentyl glycol, cyclohexanedimethanol and 4,4-N-(1-methylpropylidene)bisphenol may be used as aliphatic diols. Glycerol, pentaerythritol, sorbitol and trimethylolpropane may be used as polyols.

The polyesteramides may be obtained in a similar manner to the polyesters, by polycondensation of diacids with diamines or amino alcohols. Ethylenediamine, hexamethylenediamine or meta- or para-phenylenediamine may be used as diamine. Monoethanolamine may be used as amino alcohol.

As monomer bearing an anionic group which may be used during the polycondensation, mention may be made, for example, of dimethylolpropionic acid, trimellitic acid or a derivative such as trimellitic anhydride, the sodium salt of pentanediol-3-sulphonic acid and the sodium salt of 5-sulpho-1,3-benzenedicarboxylic acid. The fatty-chain polyesters may be obtained using fatty-chain diols during the polycondensation. The epoxy ester resins may-be obtained by polycondensation of fatty acids with a condensate having α,ω-diepoxy ends.

The free-radical polymers may in particular be acrylic and/or vinyl polymers or copolymers. Anionic radical polymers are preferred. As a monomer bearing an anionic group which may be used during the free-radical polymerization, mention may be made of acrylic acid, methacrylic acid, crotonic acid, maleic anhydride or 2-acrylamido-2-methylpropanesulphonic acid.

The acrylic polymers may result from the copolymerization of monomers selected from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide.

Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate, are preferably used.

The vinyl polymers may result from the homopolymerization or copolymerization of monomers selected from vinyl esters, styrene or butadiene. As examples of vinyl esters, mention may be made of vinyl acetate, vinyl neodecanoate, vinyl pivalate, vinyl benzoate and vinyl t-butylbenzoate.

Acrylic/silicone copolymers or even nitrocellulose/acrylic copolymers may also be used.

The polymers of natural origin, which are optionally modified, may be selected from shellac, sandarac gum, dammar resins, elemi gums, copal resins, cellulose derivatives, and mixtures thereof.

Mention may also be made of the polymers resulting from the free-radical polymerization of one or more free-radical monomers inside and/or partially at the surface of preexisting particles of at least one polymer selected from the group consisting of polyurethanes, polyureas, polyesters, polyesteramides and/or alkyds. These polymers are generally referred to as "hybrid polymers".

When an aqueous dispersion of polymer particles is used, the solids content of the said aqueous dispersion may be from about 5% to 60% and preferably from 30% to 50% by weight.

The size of the polymer particles in aqueous dispersion may be between 10 and 500 nm and is preferably between 20 and 150 nm, allowing the production of a film of noteworthy gloss. However, particle sizes ranging up to 1 micron may be used.

Aqueous dispersions of film-forming polymers that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ by the company Daito Kasey Kogyo; Syntran 5760 by the company Interpolymer or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulphopolyesters sold under the brand name Eastman AQ® by the company Eastman Chemical Products, and vinyl dispersions, for instance Mexomere PAM.

Water-soluble Polymers:

In the case where the composition comprises an aqueous phase, the film-forming polymer may be a water-soluble polymer. The water-soluble polymer is thus dissolved in the aqueous phase of the composition.

Among the water-soluble film-forming polymers that may be mentioned are the following cationic polymers:

(1) acrylic polymers or copolymers, such as polyacrylates or polymethacrylates; the copolymers of the family (1) may also contain one or more units derived from comonomers that may be selected from the family of acrylamides, methacrylamides, diacetoneacrylamides, acrylamides and methacrylamides substituted on the nitrogen by lower alkyls, acrylic or methacrylic acids or esters thereof, vinyllactams such as vinylpyrrolidone or vinylcaprolactam, or vinyl esters.

Thus, among these copolymers of the family (1), mention may be made of:

copolymers of acrylamide and of dimethylaminoethyl methacrylate, quaternized with dimethyl sulphate or with a dimethyl halide, such as the product sold under the name Hercofloc by the company Hercules, the copolymer of acrylamide and of methacryloyloxyethyltrimethylammonium chloride. described, for example, in patent application EP080976A and sold under the name Bina Quat P 100 by the company Ciba Geigy, the copolymer of acrylamide and of methacryloyloxyethyltrimethylammonium methosulphate sold under the name Reten by the company Hercules, quaternized or non-quaternized copolymers of vinylpyrolidone/dialkylaminoalkyl acrylate or methacrylate, such as the. products sold under the name "Gafquat" by the company ISP, for instance "Gafquat 734" or "Gafquat 755", or alternatively the products denoted as "Copolymer 845, 958 and 937". These polymers are described in detail in French patents 2077143 and 2393573, terpolymers of dimethylaminoethyl methacrylate/vinylcaprolactam/vinylpyrrolidone, such as the product sold under the name Gaffix VC 713 by the company ISP; and the quaternized copolymer of vinyl-pyrrolidone/dimethylaminopropylmethacrylamide, such as the product sold under the name "Gafquat HS 100" by the company ISP;

(2) the quaternized polysaccharides described more particularly in patents U.S. Pat. No. 3,589,578 and U.S. Pat. No. 4,031,307, the entire contents of which are hereby incorporated by reference, such as guar gums containing trialkylammonium cationic groups. Such products are sold in particular under the trade names Jaguar C13 S, Jaguar C 15 and Jaguar C 17 by the company Meyhall;

(3) quaternary copolymers of vinylpyrrolidone and of vinylimidazole;

(4) chitosans or salts thereof;

(5) cationic cellulose derivatives such as copolymers of cellulose or of cellulose derivatives grafted with a water-soluble monomer comprising a quaternary ammonium, and described in particular in patent U.S. Pat. No. 4,131,576, the entire contents of which is hereby incorporated by reference, such as hydroxyalkylcelluloses, for instance hydroxymethyl-, hydroxyethyl- or hydroxy-propylcelluloses grafted in particular with a meth-acryloyloxyethyltrimethylammonium, methacrylamido-propyltrimethylammonium or dimethyldiallylammonium salt. The products sold corresponding to this definition are, more particularly, the products sold under the name "Celquat L 200" and "Celquat H 100" by the National Starch Company.

Among the film-forming water-soluble polymers that may be mentioned are the following amphoteric polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkyl-aminoalkyl methacrylate and acrylate, dialkylamino-alkylmethacrylamide and -acrylamide. Such compounds are described in patent U.S. Pat. No. 3,836,537, the entire content of which is hereby incorporated by reference;

(2) polymers comprising units derived from:
 a) at least one monomer selected from acrylamides and methacrylamides substituted on the nitrogen with an alkyl radical,
 b) at least one acidic comonomer containing one or more reactive carboxylic groups, and
 c) at least one basic comonomer such as esters containing primary, secondary, tertiary and quaternary amine substituents of acrylic and methacrylic acids, and the product of quaternization of dimethylaminoethyl methacrylate with dimethyl or diethyl sulphate;

(3) crosslinked alkylpolyaminoamides totally or partially derived from polyaminoamides;

(4) polymers comprising zwitterionic units;

(5) chitosan-derived polymer;

(6) polymers derived from the N-carboxy-alkylation of chitosan, such as N-carboxymethylchitosan or N-carboxybutylchitosan sold under the name "Evalsan" by the company Jan Dekker;

(7) ($C_1$-$C_5$)alkyl vinyl ether/maleic anhydride copolymers, partially modified by a semi-amidation with an N,N-dialkylaminoalkylamine, such as N,N-dimethylaminopropylamine, or by a semi-esterification with an N,N-dialkanolamine. These copolymers may also comprise other vinyl comonomers, such as vinylcaprolactam.

The water-soluble film-forming polymers are preferably chosen from:

proteins, for instance proteins of plant origin, such as wheat proteins and soya proteins; proteins of animal origin, such as keratin, for example keratin hydrolysates and sulphonic keratins;

anionic, cationic, amphoteric or nonionic chitin or chitosan polymers;

cellulosic polymers, such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates;

vinyl polymers, for instance polyvinylpyrrolidones, copolymers of methyl vinyl ether and of maleic anhydride, the copolymer of vinyl acetate and of crotonic acid, copolymers of vinylpyrrolidone and of vinyl acetate;

copolymers of vinylpyrrolidone and of caprolactam; polyvinyl alcohols;

polymers of natural origin, which are optionally modified, such as:

gum arabic, guar gum, xanthan derivatives, karaya gum;

alginates and carrageenans;

glycosaminoglycans, hyaluronic acid and derivatives thereof;

shellac, sandarac gum, dammar resins, elemi gums and copal resins;

deoxyribonucleic acid;

mucopolysaccharides such as hyaluronic acid and chondroitin sulphate, and mixtures thereof.

These polymers will be used in particular if a more or less appreciable removal of the film by water is desired.

Other Types of Film-forming Polymers:

In order to improve the film-forming nature of an oily or aqueous polymer, it is possible to add to the polymer system a coalescer, which will be selected from the known coalescers.

According to one embodiment of the invention, the film-forming polymer may be selected from polymers containing a non-silicone organic skeleton grafted with monomers containing a polysiloxane. These polymers may be fat-soluble, lipodispersible, water-soluble or dispersible in aqueous medium, where appropriate.

The polymers containing a non-silicone organic skeleton grafted with monomers containing a polysiloxane consist of an organic main chain formed from organic monomers not comprising silicone, onto which is grafted, within the said chain and also optionally on at least one of its ends, at least one polysiloxane macromer.

In the text hereinbelow, in accordance with what is generally accepted, the expression "polysiloxane macromer" is understood to refer to any monomer containing a polysiloxane-type polymer chain in its structure.

The non-silicone organic monomers constituting the main chain of the grafted silicone polymer can be selected from free-radically polymerizable monomers containing ethylenic unsaturation, polycondensation-polymerizable monomers, such as those forming polyamides, polyesters or polyurethanes, and ring-opening monomers, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the free-radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably selected from those described in patents U.S. Pat. No. 4,693,935, U.S. Pat. No. 4,728,571 and U.S. Pat. No. 4,972,037 and patent applications EP0412704A, EP0412707A, EP0640105A and WO95/00578, the entire contents of which are hereby incorporated by reference. These are copolymers obtained by free-radical polymerization starting with monomers containing ethylenic unsaturation and monomers having a terminal vinyl group, or alternatively copolymers obtained by reaction of a polyolefin comprising functionalized groups and a polysiloxane macromer having a terminal function which is reactive with the said functionalized groups.

One particular family of grafted silicone polymers which is suitable for carrying out the present invention consists of grafted silicone polymers comprising:

a) from 0% to 98% by weight of at least one free-radically polymerizable lipophilic monomer (A) of low polarity containing ethylenic unsaturation;
 b) from 0% to 98% by weight of at least one polar hydrophilic monomer (B) containing ethylenic unsaturation, which is copolymerizable with the monomer(s) of the type (A);

c) from 0.01% to 50% by weight of at least one polysiloxane macromer (C) of general formula:

$$X(Y)_n Si(R)_{3-m} Z_m \quad (I)$$

in which:
X denotes a vinyl group which is copolymerizable with the monomers (A) and (B);
Y denotes a divalent bonding group;
R denotes hydrogen, $C_1$-$C_6$ alkyl or alkoxy, or $C_6$-$C_{12}$ aryl;
Z denotes a monovalent polysiloxane unit with a number-average molecular weight of at least 500;
n is 0 or 1 and m is an integer ranging from 1 to 3; the percentages being calculated relative to the total weight of the monomers (A), (B) and (C).

These polymers have a number-average molecular weight ranging from 10,000 to 2,000,000 and preferably a glass transition temperature $T_g$ or a crystalline melting temperature $T_m$ of at least −20° C.

As examples of lipophilic monomers (A), mention may be made of acrylic or methacrylic acid esters of $C_1$-$C_{18}$ alcohols; methacrylic acid esters of $C_{12}$-$C_{30}$ alcohols, styrene; polystyrene macromers; vinyl acetate; vinyl propionate; alpha-methylstyrene; tert-butylstyrene; butadiene; cyclohexadiene; ethylene; propylene; vinyltoluene; acrylic or methacrylic acid esters of 1,1-dihydroperfluoroalkanols or of homologues thereof; acrylic or methacrylic acid esters of omega-hydrofluoroalkanols; acrylic or methacrylic acid esters of fluoroalkylsulphonamido alcohols; acrylic or methacrylic acid esters of fluoroalkyl alcohols; acrylic or methacrylic acid esters of fluoroether alcohols; or mixtures thereof. The preferred monomers (A) are selected from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(N-butylperfluorooctane sulphonamido)ethyl acrylate, and mixtures thereof.

As examples of polar monomers (B), mention may be made of acrylic acid, methacrylic acid, N,N-dimethylacrylamide, dimethylaminoethyl methacrylate, quatemized dimethylaminoethyl methacrylate, (meth)acrylamide, N-t-butylacrylamide, maleic acid, maleic anhydride and hemiesters thereof, hydroxyalkyl(meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinylcaprolactam, or mixtures thereof. The preferred monomers (B) are selected from the group consisting of acrylic acid, N,N-dimethylacrylamide, dimethylaminoethyl methacrylate, quaternized dimethylaminoethyl methacrylate and vinylpyrrolidone, and mixtures thereof.

Mention is made especially of the product KP 561 or KP 562 sold by Shin Etsu such that the monomer (A) is selected from esters of a $C_{18}$-$C_{22}$ alcohol and of methacrylic acid.

The polysiloxane macromers (C) of formula (I) are selected preferably from those corresponding to the general formula (II) below:

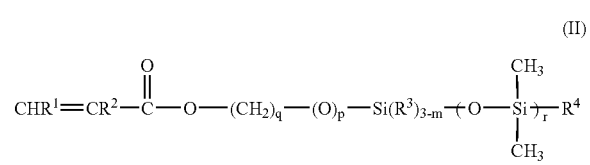

(II)

in which:
$R^1$ is hydrogen or —COOH (preferably hydrogen);
$R^2$ is hydrogen, methyl or —$CH_2COOH$ (preferably methyl);
$R^3$ is $C_1$-$C_6$ alkyl, alkoxy or alkylamino, $C_6$-$C_{12}$ aryl or hydroxyl (preferably methyl);
$R^4$ is $C_1$-$C_6$ alkyl, alkoxy or alkylamino, $C_6$-$C_{12}$ aryl or hydroxyl (preferably methyl);
q is an integer from 2 to 6 (preferably 3);
p is 0 or 1;
r is an integer from 5 to 700;
m is an integer from 1 to 3 (preferably 1).

Preference is given to using the polysiloxane macromers of formula:

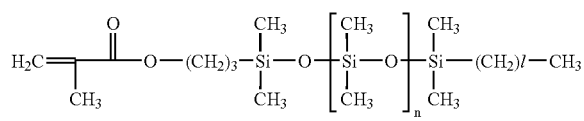

with n being a number ranging from 5 to 700 and l being an integer between 0 and 3.

One embodiment of the invention consists in using a copolymer which may be obtained by free-radical polymerization starting from the monomer mixture consisting of:
a) 60% by weight of tert-butyl acrylate;
b) 20% by weight of acrylic acid;
c) 20% by weight of silicone macromer of formula:

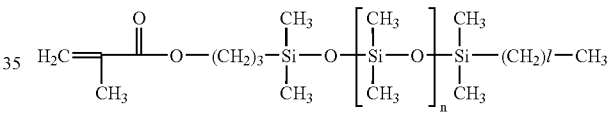

with n being a number ranging from 5 to 700 and l being an integer between 0 and 3, the weight percentages being calculated relative to the total weight of the monomers.

Another particular embodiment of the invention consists in using a copolymer which may be obtained by free-radical polymerization starting from the monomer mixture consisting of:
a) 80% by weight of tert-butyl acrylate;
b) 20% by weight of silicone macromer of formula:

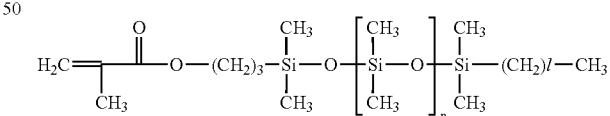

with n being a number ranging from 5 to 700 and l being an integer between 0 and 3, the weight percentages being calculated relative to the total weight of the monomers.

Another particular family of grafted silicone polymers containing a non-silicone organic skeleton that is suitable for carrying out the present invention consists of grafted silicone copolymers which may be obtained by reactive extrusion-molding of a polysiloxane macromer with a reactive terminal function on a polymer of the polyolefin type comprising reactive groups capable of reacting with the terminal function of the polysiloxane macromer to form a covalent bond for grafting the silicone onto the main chain of the polyolefin. These polymers are described, along with a process for their preparation, in patent application WO95/00578, the entire content of which is hereby incorporated by reference.

The reactive polyolefins are preferably selected from polyethylenes and polymers of ethylene-derived monomers such as propylene, styrene, alkyl-styrene, butylene, butadiene, (meth)acrylates, vinyl esters or equivalents, comprising reactive functions capable of reacting with the terminal function of the polysiloxane macromer. They are selected more particularly from copolymers of ethylene or of ethylene derivatives and of monomers selected from those comprising a carboxylic function such as (meth)acrylic acid; those comprising an acid anhydride function such as maleic anhydride; those comprising an acid chloride function such as (meth)acryloyl chloride; those comprising an ester function such as (meth)acrylic acid esters; those comprising an isocyanate function.

The silicone macromers are preferably selected from polysiloxanes comprising a functionalized group, at the end of the polysiloxane chain or close to the end of the said chain, selected from the group consisting of alcohols, thiols, epoxy groups and primary and secondary amines, and more particularly from those corresponding to the general formula:

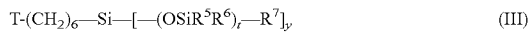

$$T\text{-}(CH_2)_6\text{---}Si\text{---}[\text{---}(OSiR^5R^6)_t\text{---}R^7]_y \quad (III)$$

in which T is selected from the group consisting of $NH_2$, NHRN and an epoxy, OH, or SH function; $R^5$, $R^6$, $R^7$ and RN independently denote a $C_1$-$C_6$ alkyl, phenyl, benzyl, or $C_6$-$C_{12}$ alkylphenyl or hydrogen; s is a number from 2 to 100; t is a number from 0 to 1,000 and y is a number from 1 to 3. They have a number-average molecular weight preferably ranging from 5,000 to 300,000, more preferably from 8,000 to 200,000 and more particularly from 9,000 to 40,000.

According to one preferred embodiment, the film-forming polymer may be purchased from the Minnesota Mining and Manufacturing Company under the trade names of "Silicone Plus" polymers. For example, poly(isobutyl methacrylate-co-methyl FOSEA)-g-poly(dimethylsiloxane) is sold under the trade name SA 70-5 IBMMF.

According to another preferred form of the invention, the film-forming polymer is selected from silicone polymers grafted with non-silicone organic monomers. These polymers may be fat-soluble, fat-dispersible, water-soluble or dispersible in aqueous medium, where appropriate.

The said grafted silicone polymer(s) containing a polysiloxane skeleton grafted with non-silicone organic monomers comprise a silicone (or polysiloxane (/SiO—$)_n$) main chain onto which is grafted, within the said chain and also optionally on at least one of its ends, at least one organic group not comprising silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between /Si—H groups and vinyl groups $CH_2$=CH—, or alternatively the reaction between thio functional groups —SH with these same vinyl groups.

Examples of polymers containing a polysiloxane skeleton grafted with non-silicone organic monomers that are suitable for carrying out the present invention, and also their specific mode of preparation, are described in particular in patent applications EP0582152A, WO93/23009 and WO95/03776, the entire contents of which are hereby incorporated by reference.

According to a particularly preferred embodiment of the present invention, the silicone polymer containing a polysiloxane skeleton grafted with non-silicone organic monomers which is used comprises the result of a free-radical copolymerization between, on the one hand, at least one non-silicone anionic organic monomer containing ethylenic unsaturation and/or a non-silicone hydrophobic organic monomer containing ethylenic unsaturation, and, on the other hand, a silicone containing in its chain at least one, and preferably several, functional group(s) capable of reacting with the said ethylenic unsaturations of the said non-silicone monomers, forming a covalent bond, in particular thio functional groups.

According to the present invention, the said anionic monomers containing ethylenic unsaturation are preferably selected, alone or as mixtures, from linear or branched, unsaturated carboxylic acids, optionally partially or totally neutralized in the form of a salt, it being possible for this or these unsaturated carboxylic acid(s) to be, more particularly, acrylic acid, methacrylic acid, maleic acid, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the free-radical (homo)polymerization of at least one anionic monomer of unsaturated carboxylic acid type can, after reaction, be post-neutralized with a base (sodium hydroxide, aqueous ammonia, etc.) in order to turn it into a salt.

According to the present invention, the hydrophobic monomers containing ethylenic unsaturation are preferably selected, alone or as mixtures, from acrylic acid esters of alkanols and/or methacrylic acid esters of alkanols. The alkanols are preferably $C_1$-$C_{30}$ and more particularly $C_1$-$C_{22}$. The preferred monomers are selected from the group consisting of isooctyl(meth)acrylate, isononyl(meth)acrylate, 2-ethylhexyl(meth)acrylate, lauryl(meth)acrylate, isopentyl(meth)acrylate, n-butyl(meth)acrylate, isobutyl(meth)acrylate, methyl(meth)acrylate, tert-butyl(meth)acrylate, tridecyl(meth)acrylate and stearyl(meth)acrylate, or mixtures thereof.

One family of silicone polymers containing a polysiloxane skeleton grafted with non-silicone organic monomers that is particularly suitable for carrying out the present invention consists of silicone polymers comprising in their structure the unit of formula IV below:

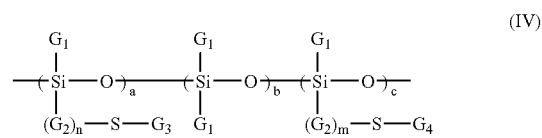

in which the radicals $G_1$, which are identical or different, represent hydrogen, a $C_1$-$C_{10}$ alkyl radical or a phenyl radical; the radicals $G_2$, which may be identical or different, represent a $C_1$-$C_{10}$ alkylene group; $G_3$ represents a polymer residue resulting from the (homo)polymerization of at least one anionic monomer containing ethylenic unsaturation; $G_4$ represents a polymer residue resulting from the (homo)-polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) of the above text has at least one, and even more preferably all, of the following characteristics:
  the radicals $G_1$ denote an alkyl radical, preferably a methyl radical;
  n is not zero, and the radicals $G_2$ represent a divalent $C_1$-$C_3$ radical, preferably a propylene radical;
  $G_3$ represents a polymer radical resulting from the (homo) polymerization of at least one monomer of the carboxylic acid type containing ethylenic unsaturation, preferably acrylic acid and/or methacrylic acid;
  $G_4$ represents a polymer radical resulting from the homo polymerization of at least one monomer of the $C_1$-$C_{10}$ alkyl(meth)acrylate type, preferably isobutyl or methyl (meth)acrylate.

Examples of silicone polymers corresponding to the formula (IV) are, in particular, polydimethyl-siloxanes (PDMSs) onto which are grafted, via a thiopropylene-type connecting chain, mixed polymer units of the poly(meth)acrylic acid type and of the polyalkyl(meth)acrylate type.

Other examples of silicone polymers corresponding to formula (IV) are, in particular, polydimethylsiloxanes (PDMSs) onto which are grafted, via a thiopropylene-type connecting chain, polymer units of the polyisobutyl(meth)acrylate type.

Such polymers include polymers comprising at least one group of formula:

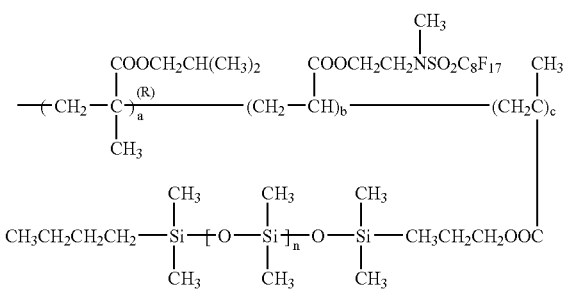

in which
a, b and c, which may be identical or different, are each a number ranging from 1 to 100,000; and the end groups, which may be identical or different, are each selected from linear $C_1$-$C_{20}$ alkyl groups, $C_3$-$C_{20}$ branched-chain alkyl groups, $C_3$-$C_{20}$ aryl groups, linear $C_1$-$C_{20}$ alkoxy groups and branched $C_3$-$C_{20}$ alkoxy groups.

Such polymers are disclosed in patents U.S. Pat. No. 4,972,037, U.S. Pat. No. 5,061,481, U.S. Pat. No. 5,209,924, U.S. Pat. No. 5,849,275, U.S. Pat. No. 6,033,650 and patent applications WO93/23446 and WO95/06078, the entire contents of which are hereby incorporated by reference.

Another family of silicone polymers having a polysiloxane skeleton grafted with non-silicone organic monomers, which is particularly suitable for performing the present invention, consists of silicone polymers comprising in their structure the unit of formula (V) below:

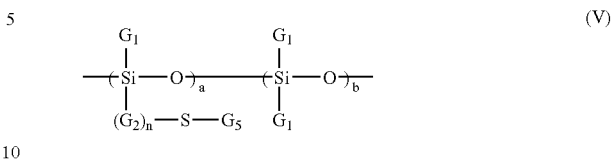

in which the radicals $G_1$ and $G_2$ have the same meaning as above; $G_5$ represents a polymer residue resulting from the (homo)-polymerization of at least one ethylenically unsaturated hydrophobic monomer or from the copolymerization of at least one ethylenically unsaturated anionic monomer and of at least one ethylenically unsaturated hydrophobic monomer; n is equal to 0 or 1; a is an integer ranging from 0 to 50; b is an integer that may be between 10 and 350; on condition that a is other than 0.

The unit of formula (V) in the above text preferably has at least one, and even more preferably all, of the following characteristics:
  the radicals $G_1$ denote an alkyl radical, preferably a methyl radical;
  n is not zero, and the radicals $G_2$ represent a $C_1$-$C_3$ divalent radical, preferably a propylene radical.

The number-average molecular mass of the silicone polymers with a polysiloxane skeleton grafted with non-silicone organic monomers of the invention preferably ranges from about 10,000 to 1,000,000 and even more preferably from about 10,000 to 100,000.

Still other film formers may be in the form of a cyclized dimethicone. The term "cyclized dimethicone" means an organosiloxane comprised of repeating —[Si—$O_{2/2}$]—, or "D" units, which form one or more cyclized portions in the final polymer. The cyclized portions, or rings, are formed by crosslinking certain portions along the organosiloxane chain to form rings that may be structurally aligned along the polymeric chain in the manner depicted below:

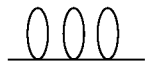

Preferably, the rings in the polymer have a molecular weight ranging from about 40,000 to 50,000, more preferably about 45,000, with the final polymer having a molecular weight ranging from about 1.6 to 2.6, preferably about 2.0 million. Cyclized dimethicone may be purchased from Jeen International under the tradename JEESILC IDD which is a mixture of cyclized dimethicone (having the INCI name dimethicone crosspolymer-3) and isododecane; or JEECHEM HPIB which is a mixture of cyclized dimethicone (dimethicone crosspolymer-3) and hydrogenated polyisobutene and cyclomethicone.

Block Polymers Suitable as Film-forming Polymers:

The term "ethylenic polymer" means a polymer obtained by polymerization of monomers comprising an ethylenic unsaturation.

The term "block polymer" means a polymer comprising at least two different blocks and preferably at least three different blocks.

The film-forming polymer may also be a film-forming linear ethylenic block polymer, which is advantageously free of styrene. More preferably, the block polymer comprises at least two blocks which are mutually incompatible and have different glass transition temperatures ($T_g$), the two blocks being linked together via an intermediate block comprising at least one constituent monomer of the first block and at least one constituent monomer of the second block.

The polydispersity index I of the polymer is equal to the ratio of the weight-average mass Mw to the number-average mass Mn. The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer used in the composition according to the invention is preferably less than or equal to 300,000; it ranges, for example, from 35,000 to 200,000 and better still from 45,000 to 150,000.

The number-average mass (Mn) of the polymer used in the composition according to the invention is preferably less than or equal to 70,000; it ranges, for example, from 10,000 to 60,000 and better still from 12,000 to 50,000.

The polydispersity index of the block polymer of the present invention is greater than 2, for example greater than 2 and less than or equal to 9, preferably greater than or equal to 2.5, for example ranging from 2.5 to 8, and better still greater than or equal to 2.8, especially from 2.8 to 6.

Examples of suitable block polymers include, but are not limited to, those described in the French patent application filed under the number 0311337, the entire content of which is hereby incorporated by reference.

The term "mutually incompatible" means that the blend formed by mixing the at least two blocks is not miscible in the organic liquid that is the majority amount by weight of the organic liquid medium of the composition, at room temperature (25° C.) and atmospheric pressure ($10^5$ Pa), for a polymer blend content of greater than or equal to 5% by weight, relative to the total weight of the blend (polymers and solvent), it being understood that:

i) the said polymers are present in the blend in a content such that the respective weight ratio ranges from 10/90 to 90/10, and ii) each of the polymers corresponding to the first and second blocks has an average (weight-average or number-average) molecular mass equal to that of the block polymer±15%.

In the case where the organic liquid medium comprises a mixture of organic liquids, and should two or more organic liquids be present in identical mass proportions, the said polymer blend is immiscible in at least one of them.

Needless to say, in the case where the organic liquid medium comprises only one organic liquid, this liquid is the majority organic liquid.

Advantageously, the majority organic liquid of the composition is the organic solvent for polymerization of the block polymer or the majority organic solvent of the mixture of organic solvents for polymerization of the block polymer.

The intermediate block is a block comprising at least one constituent monomer of the at least two block (co)polymer which enables it to "compatibilize" the at least two mutually incompatible blocks.

Preferably, the polymer used in the composition according to the invention does not comprise any silicon atoms in its skeleton. The term "skeleton" means the main chain of the polymer, as opposed to the pendent side chains.

Preferably, the polymer used in the composition according to the invention is not water-soluble, i.e. the polymer is not soluble in water or in a mixture of water and of linear or branched lower monoalcohols containing from 2 to 5 carbon atoms, for instance ethanol, isopropanol or n-propanol, without pH modification, at an active material content of at least 1% by weight, at room temperature (25° C.).

Advantageously, the block polymer used according to the invention is present in the organic liquid medium of the composition.

Preferably, the polymer used in the composition according to the invention is non-elastomeric.

The term "non-elastomeric" means that when the polymer is subjected to a constraint intended to stretch it (for example by 30% relative to its initial length), it does not return to a length substantially identical to its initial length when the constraint ceases.

More specifically, the term "non-elastomeric" denotes a polymer with an instantaneous recovery $R_i$<50% and a delayed recovery $R_{2h}$<70% after having been subjected to a 30% elongation. Preferably, $R_i$ is <30% and $R_{2h}$<50%.

More specifically, the non-elastomeric nature of the polymer is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 μm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($I_0$) of the specimen.

The instantaneous recovery $R_i$ is determined in the following manner:

the specimen is pulled by 30% ($\epsilon_{max}$), i.e. about 0.3 times its initial length ($I_0$)

the constraint is released by applying a return speed equal to the tensile speed, i.e. 50 mm/min, and the residual elongation of the specimen is measured as a percentage, after returning to zero constraint ($\epsilon_i$).

The percentage instantaneous recovery ($R_i$) is given by the following formula:

$$R_i = (\epsilon_{max} - \epsilon_i)/\epsilon_{max} \times 100$$

To determine the delayed recovery, the percentage residual elongation of the specimen ($\epsilon_{2h}$) is measured.

The percentage delayed recovery ($R_{2h}$) is given by the following formula:

$$R_{2h} = (\epsilon_{max} - \epsilon_{2h})/\epsilon_{max} \times 100$$

Purely as a guide, a polymer according to one embodiment of the invention has an instantaneous recovery $R_i$ of 10% and a delayed recovery $R_{2h}$ of 30%.

Each block of the polymer used in the composition according to the invention is derived from one type of monomer or from several different types of monomer.

This means that each block may consist of a homopolymer or a copolymer; this copolymer constituting the block may in turn be random or alternating.

Advantageously, the intermediate block comprising at least one constituent from the at least two block (co) polymers is a random polymer.

Preferably, the intermediate block is derived essentially from constituent monomers of the at least two block (co) polymers.

The term "essentially" means at least 85%, preferably at least 90%, better still 95% and even better still 100%.

Advantageously, the intermediate block has a glass transition temperature $T_g$ that is between the glass transition temperatures of the at least two blocks.

The glass transition temperatures indicated for the first and second blocks may be theoretical $T_g$ values determined from the theoretical $T_g$ values of the constituent monomers of each of the blocks, which may be found in a reference manual such as the Polymer Handbook, 3rd Edition, 1989, John Wiley, according to the following relationship, known as Fox's law:

$$1/T_g = \sum_i (\overline{\omega}_i/T_{gi}),$$

$\overline{\omega}_i$ being the mass fraction of the monomer i in the block under consideration and $T_{gi}$ being the glass transition temperature of the homopolymer of the monomer i.

Unless otherwise indicated, the $T_g$ values indicated for the at least two blocks in the present patent application are theoretical $T_g$ values.

Advantageously, the at least two blocks of the polymer are such that the difference between the glass transition temperatures of the first and second blocks is generally greater than 10° C., preferably greater than 20° C. and better still greater than 30° C.

In particular, one block may be chosen from:
a) a block with a $T_g$ of greater than or equal to 40° C.,
b) a block with a $T_g$ of less than or equal to 20° C.,
c) a block with a $T_g$ of between 20 and 40° C.,
and the other block can be chosen from a category a), b) or c) different from the first block.

In the present invention, the expression:
"between . . . and . . . " is intended to denote a range of values for which the limits mentioned are excluded, and
"from . . . to . . . " and "ranging from . . . to . . . " are intended to denote a range of values for which the limits are included.

a) Block with a $T_g$ of Greater than or Equal to 40° C.

The block with a $T_g$ of greater than or equal to 40° C. has, for example, a $T_g$ ranging from 40 to 150° C., preferably greater than or equal to 50° C., for example ranging from 50° C. to 120° C. and better still greater than or equal to 60° C., for example ranging from 60° C. to 120° C.

The block with a $T_g$ of greater than or equal to 40° C. may be a homopolymer or a copolymer.

In the case where this block is a homopolymer, it is derived from a monomer whose homopolymer has a glass transition temperature of greater than or equal to 40° C.

In the case where the first block is a copolymer, it may be totally or partially derived from one or more monomers, the nature and concentration of which are chosen such that the $T_g$ of the resulting copolymer is greater than or equal to 40° C. The copolymer may comprise, for example:
monomers whose homopolymer has a $T_g$ value of greater than or equal to 40° C., for example a $T_g$ ranging from 40 to 150° C., preferably greater than or equal to 50° C., for example ranging from 50° C. to 120° C. and better still greater than or equal to 60° C., for example ranging from 60° C. to 120° C., and
monomers whose homopolymer has a $T_g$ value of less than 40° C., chosen from monomers whose homopolymer has a $T_g$ of between 20 and 40° C. and/or monomers whose homopolymer has a $T_g$ of less than or equal to 20° C., for example a $T_g$ ranging from −100 to 20° C., preferably less than 15° C., especially ranging from −80° C. to 15° C. and better still less than 10° C., for example ranging from −50° C. to 0° C., as described later.

The monomers whose homopolymer has a glass transition temperature of greater than or equal to 40° C. are chosen, preferably, from the following monomers, also known as the main monomers:
methacrylates of formula $CH_2=C(CH_3)-COOR_1$
in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group,
acrylates of formula $CH_2=CH-COOR_2$
in which $R_2$ represents a $C_4$ to $C_{12}$ cycloalkyl group such as an isobornyl group or a tert-butyl group,
(meth)acrylamides of formula:

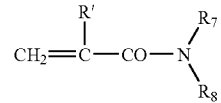

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group,
and R' denotes H or methyl. Examples of monomers that may be mentioned include N-butylacrylamide, N-t-butylacrylamide, N-isopropylacrylamide, N,N-dimethylacrylamide and N,N-dibutylacrylamide,
and mixtures thereof.

Main monomers that are particularly preferred are methyl methacrylate, isobutyl(meth)acrylate and isobornyl(meth)acrylate, and mixtures thereof.

b) Block with a $T_g$ of Less than or Equal to 20° C.

The block with a $T_g$ of less than or equal to 20° C. has, for example, a $T_g$ ranging from −100 to 20° C., preferably less than or equal to 15° C., especially ranging from −80° C. to 15° C. and better still less than or equal to 10° C., for example ranging from −50° C. to 0° C.

The block with a $T_g$ of less than or equal to 20° C. may be a homopolymer or a copolymer.

In the case where this block is a homopolymer, it is derived from monomers which are such that the homopolymers prepared from these monomers have glass transition temperatures of less than or equal to 20° C. This second block may be a homopolymer consisting of only one type of monomer (for which the $T_g$ of the corresponding homopolymer is less than or equal to 20° C.).

In the case where the block with a $T_g$ of less than or equal to 20° C. is a copolymer, it may be totally or partially derived from one or more monomers, the nature and concentration of which are chosen such that the $T_g$ of the resulting copolymer is less than or equal to 20° C.

It may comprise, for example
one or more monomers whose corresponding homopolymer has a $T_g$ of less than or equal to 20° C., for example a $T_g$ ranging from −100° C. to 20° C., preferably less than 15° C., especially ranging from −80° C. to 15° C.

and better still less than 10° C., for example ranging from −50° C. to 0° C., and one or more monomers whose corresponding homopolymer has a $T_g$ of greater than 20° C., such as monomers with a $T_g$ of greater than or equal to 40° C., for example a $T_g$ ranging from 40 to 150° C., preferably greater than or equal to 50° C., for example ranging from 50° C. to 120° C. and better still greater than or equal to 60° C., for example ranging from 60° C. to 120° C. and/or monomers with a $T_g$ of between 20 and 40° C., as described above.

Preferably, the block with a $T_g$ of less than or equal to 20° C. is a homopolymer.

The monomers whose homopolymer has a $T_g$ of less than or equal to 20° C. are preferably chosen from the following monomers, or main monomer:

acrylates of formula $CH_2$=$CHCOOR_3$, $R_3$ representing a linear or branched $C_1$ to $C_{12}$ unsubstituted alkyl group, with the exception of the tert-butyl group, in which one or more hetero atoms chosen from O, N and S is (are) optionally intercalated, methacrylates of formula $CH_2$=$C(CH_3)$—$COOR_4$, $R_4$ representing a linear or branched $C_6$ to $C_{12}$ unsubstituted alkyl group, in which one or more hetero atoms chosen from O, N and S is (are) optionally intercalated;

vinyl esters of formula $R_5$—CO—O—CH=$CH_2$ in which $R_5$ represents a linear or branched $C_4$ to $C_{12}$ alkyl group, $C_4$ to $C_{12}$ alkyl vinyl ethers, such as methyl vinyl ether and ethyl vinyl ether, N—($C_4$ to $C_{12}$)alkyl acrylamides, such as N-octylacrylamide, and mixtures thereof.

The main monomers that are particularly preferred for the block with a $T_g$ of less than or equal to 20° C. are alkyl acrylates whose alkyl chain contains from 1 to 10 carbon atoms, with the exception of the tert-butyl group, such as methyl acrylate, isobutyl acrylate and 2-ethylhexyl acrylate, and mixtures thereof.

c) Block with a $T_g$ of Between 20 and 40° C.

The block with a $T_g$ of between 20 and 40° C. may be a homopolymer or a copolymer.

In the case where this block is a homopolymer, it is derived from a monomer (or main monomer) whose homopolymer has a glass transition temperature of between 20 and 40° C.

The monomers whose homopolymer has a glass transition temperature of between 20 and 40° C. are preferably chosen from n-butyl methacrylate, cyclodecyl acrylate, neopentyl acrylate and isodecylacrylamide, and mixtures thereof.

In the case where the block with a $T_g$ of between 20 and 40° C. is a copolymer, it is totally or partially derived from one or more monomers (or main monomer) whose nature and concentration are chosen such that the $T_g$ of the resulting copolymer is between 20 and 40° C.

Advantageously, the block with a $T_g$ of between 20 and 40° C. is a copolymer totally or partially derived from:

main monomers whose corresponding homopolymer has a $T_g$ of greater than or equal to 40° C., for example a $T_g$ ranging from 40° C. to 150° C., preferably greater than or equal to 50° C., for example ranging from 50 to 120° C. and better still greater than or equal to 60° C., for example ranging from 60° C. to 120° C., as described above, and main monomers whose corresponding homopolymer has a $T_g$ of less than or equal to 20° C., for example a $T_g$ ranging from −100 to 20° C., preferably less than or equal to 15° C., especially ranging from −80° C. to 15° C. and better still less than or equal to 10° C., for example ranging from −50° C. to 0° C., as described above, the said monomers being chosen such that the $T_g$ of the copolymer forming the first block is between 20 and 40° C.

Such main monomers are chosen, for example, from methyl methacrylate, isobornyl acrylate and methacrylate, butyl acrylate and 2-ethylhexyl acrylate, and mixtures thereof.

Preferably, the proportion of the second block with a $T_g$ of less than or equal to 20° C. ranges from 10% to 85% by weight, better still from 20% to 70% and even better still from 20% to 50% by weight of the polymer.

According to one embodiment, the block polymer used in the composition according to the invention is free of styrene. The term "polymer free of styrene" means a polymer comprising less than 10%, preferably less than 5%, preferably less than 2% and more preferably less than 1% by weight of, or completely free of, styrene monomers such as styrene or styrene derivatives, for instance methylstyrene, chlorostyrene or chloromethylstyrene.

According to one embodiment, the block polymer of the composition according to the invention is derived from aliphatic ethylenic monomers. The term "aliphatic monomer" means a monomer comprising no aromatic groups.

However, each of the blocks may contain in small proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from:
a) hydrophilic monomers such as:
ethylenically unsaturated monomers comprising at least one carboxylic or sulfonic acid function, for instance:
acrylic acid, methacrylic acid, crotonic acid, maleic anhydride, itaconic acid, fumaric acid, maleic acid, acrylamidopropanesulfonic acid, vinylbenzoic acid, vinylphosphoric acid, and salts thereof,
ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof,
methacrylates of formula $CH_2$=$C(CH_3)$—$COOR_6$
in which $R_6$ represents a linear or branched alkyl group containing from 1 to 4 carbon atoms, such as a methyl, ethyl, propyl or isobutyl group, the said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate,
methacrylates of formula $CH_2$=$C(CH_3)$—$COOR_9$,
$R_9$ representing a linear or branched $C_6$ to $C_{12}$ alkyl group in which one or more hetero atoms chosen from O, N and S is (are) optionally intercalated, the said alkyl group being substituted with one or more substituents chosen from hydroxyl groups and halogen atoms (Cl, Br, I or F);
acrylates of formula $CH_2$=$CHCOOR_{10}$, $R_{10}$ representing a linear or branched $C_1$ to $C_{12}$ alkyl group substituted with one or more substituents chosen from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit 5 to 30 times, for example methoxy-POE, or $R_{10}$ represents a polyoxyethylenated group comprising from 5 to 30 ethylene oxide units b) ethylenically unsaturated monomers comprising one or more silicon atoms, such as methacryloxypropyltrimethoxysilane and methacryloxypropyltris(trimethylsiloxy)silane, and mixtures thereof.

Additional monomers that are particularly preferred are acrylic acid, methacrylic acid and trifluoroethyl methacrylate, and mixtures thereof.

This or these additional monomer(s) generally represent(s) an amount of less than or equal to 30% by weight, for example from 1% to 30% by weight, preferably from 5% to 20% by weight and more preferably from 7% to 15% by weight, relative to the total weight of the first and/or second blocks.

According to one preferred embodiment, the block polymer used in the composition according to the invention is a non-silicone polymer, i.e. a polymer free of silicon atoms.

Preferably, each of the at least two blocks comprises at least one monomer chosen from (meth)acrylic acid esters as defined above and optionally one monomer chosen from (meth)acrylic acid, and mixtures thereof.

Advantageously, each of the at least two blocks is exclusively derived from at least one monomer chosen from (meth)acrylic acid esters as defined above and optionally one chosen monomer from (meth)acrylic acid, and mixtures thereof.

The polymer used in the composition according to the invention may be obtained by free-radical solution polymerization according to the following preparation process:

a portion of the polymerization solvent is introduced into a suitable reactor and heated until the adequate temperature for the polymerization is reached (typically between 60 and 120° C.), once this temperature is reached, the constituent monomers of the first block are introduced in the presence of some of the polymerization initiator, after a time T corresponding to a maximum degree of conversion of 90%, the constituent monomers of the second block and the rest of the initiator are introduced, the mixture is left to react for a time T' (ranging from 3 to 6 hours), after which the mixture is cooled to room temperature, the polymer dissolved in the polymerization solvent is obtained.

The term "polymerization solvent" means a solvent or a mixture of solvents. The polymerization solvent may be chosen especially from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to a first embodiment, the block polymer used in the composition according to the invention comprises at least one (especially one) first block with a $T_g$ of greater than or equal to 40° C., as described above in a) and at least one (especially one) second block with a $T_g$ of less than or equal to 20° C., as described above in b).

Preferably, the first block with a $T_g$ of greater than or equal to 40° C. is a copolymer derived from monomers whose homopolymer has a glass transition temperature of greater than or equal to 40° C., such as the monomers described above.

Advantageously, the second block with a $T_g$ of less than or equal to 20° C. is a homopolymer especially derived from monomers as described above.

Preferably, the proportion of the block with a Tg of greater than or equal to 40° C. ranges from 20% to 90%, better still from 30% to 80% and even better still from 50% to 70% by weight of the polymer.

Preferably, the proportion of the block with a $T_g$ of less than or equal to 20° C. ranges from 5% to 75%, preferably from 15% to 50% and better still from 25% to 45% by weight of the polymer.

Thus, according to a first variant, the polymer used in the composition according to the invention may comprise:

a first block with a $T_g$ of greater than or equal to 40° C., for example having a $T_g$ ranging from 70 to 110° C., which is a methyl methacrylate/acrylic acid copolymer, a second block with a $T_g$ of less than or equal to 20° C., for example ranging from 0 to 20° C., which is a methyl acrylate homopolymer, and an intermediate block that is a methyl methacrylate/acrylic acid/methyl acrylate copolymer.

According to a second variant, the polymer used in the composition according to the invention may comprise:

a first block with a $T_g$ of greater than or equal to 40° C., for example ranging from 70 to 100° C., which is a methyl methacrylate/acrylic acid/trifluoroethyl methacrylate copolymer, a second block with a $T_g$ of less than or equal to 20° C., for example ranging from 0 to 20° C., which is a methyl acrylate homopolymer, and an intermediate block that is a methyl methacrylate/acrylic acid/methyl acrylate/trifluoroethyl methacrylate random copolymer.

According to a third variant, the polymer used in the composition according to the invention may comprise:

a first block with a $T_g$ of greater than or equal to 40° C., for example ranging from 85 to 115° C., which is an isobornyl acrylate/isobutyl methacrylate copolymer, a second block with a $T_g$ of less than or equal to 20° C., for example ranging from −85 to −55° C., which is a 2-ethylhexyl acrylate homopolymer, and an intermediate block, which is an isobornyl acrylate/isobutyl methacrylate/2-ethylhexyl acrylate random copolymer.

According to a fourth variant, the polymer used in the composition according to the invention may comprise:

a first block with a $T_g$ of greater than or equal to 40° C., for example ranging from 85 to 115° C., which is an isobornyl acrylate/methyl methacrylate copolymer, a second block with a $T_g$ of less than or equal to 20° C., for example ranging from −85 to −55° C., which is a 2-ethylhexyl acrylate homopolymer, and an intermediate block that is an isobornyl acrylate/methyl methacrylate/2-ethylhexyl acrylate random copolymer.

According to a fifth variant, the polymer used in the composition according to the invention may comprise:

a first block with a $T_g$ of greater than or equal to 40° C., for example ranging from 95 to 125° C., which is an isobornyl acrylate/isobornyl methacrylate copolymer, a second block with a $T_g$ of less than or equal to 20° C., for example ranging from −85 to −55° C., which is a 2-ethylhexyl acrylate homopolymer, and an intermediate block that is an isobornyl acrylate/ isobornyl methacrylate/2-ethylhexyl acrylate random copolymer.

According to a sixth variant, the polymer used in the composition according to the invention may comprise:
- a first block with a $T_g$ of greater than or equal to 40° C., for example ranging from 85 to 115° C., which is an isobornyl methacrylate/isobutyl methacrylate copolymer,
- a second block with a $T_g$ of less than or equal to 20° C., for example ranging from −35 to −5° C., which is an isobutyl acrylate homopolymer, and
- an intermediate block that is an isobornyl methacrylate/ isobutyl methacrylate/isobutyl acrylate random copolymer.

According to a seventh variant, the polymer used in the composition according to the invention may comprise:
- a first block with a $T_g$ of greater than or equal to 40° C., for example ranging from 95 to 125° C., which is an isobornyl acrylate/isobornyl methacrylate copolymer,
- a second block with a $T_g$ of less than or equal to 20° C., for example ranging from −35 to −5° C., which is an isobutyl acrylate homopolymer, and
- an intermediate block that is an isobornyl acrylate/ isobornyl methacrylate/isobutyl acrylate random copolymer.

According to an eighth variant, the polymer used in the composition according to the invention may comprise:
- a first block with a $T_g$ of greater than or equal to 40° C., for example ranging from 60 to 90° C., which is an isobornyl acrylate/isobutyl methacrylate copolymer,
- a second block with a $T_g$ of less than or equal to 20° C., for example ranging from −35 to −5° C., which is an isobutyl acrylate homopolymer, and
- an intermediate block that is an isobornyl acrylate/isobutyl methacrylate/isobutyl acrylate random copolymer.

According to a second embodiment, the polymer used in the composition according to the invention comprises at least one (especially one) first block with a glass transition temperature ($T_g$) of between 20 and 40° C., in accordance with the blocks described in c) and at least one (especially one) second block with a glass transition temperature of less than or equal to 20° C., as described above in b) or a glass transition temperature of greater than or equal to 40° C., as described in a) above.

Preferably, the proportion of the first block with a $T_g$ of between 20 and 40° C. ranges from 10% to 85%, better still from 30% to 80% and even better still from 50% to 70% by weight of the polymer.

When the second block is a block with a $T_g$ of greater than or equal to 40° C., it is preferably present in a proportion ranging from 10% to 85% by weight, better still from 20% to 70% and even better still from 30% to 70% by weight of the polymer.

When the second block is a block with a $T_g$ of less than or equal to 20° C., it is preferably present in a proportion ranging from 10% to 85% by weight, better still from 20% to 70% and even better still from 20% to 50% by weight of the polymer.

Preferably, the first block with a $T_g$ of between 20 and 40° C. is a copolymer derived from monomers which are such that the corresponding homopolymer has a $T_g$ of greater than or equal to 40° C., and from monomers which are such that the corresponding homopolymer has a $T_g$ of less than or equal to 20° C.

Advantageously, the second block with a $T_g$ of less than or equal to 20° C. or with a $T_g$ of greater than or equal to 40° C. is a homopolymer.

Thus, according to a first variant of this second embodiment, the polymer used in the composition according to the invention may comprise:
- a first block with a $T_g$ of between 20 and 40° C., for example with a $T_g$ of 25 to 39° C., which is a copolymer comprising at least one methyl acrylate monomer, at least one methyl methacrylate monomer and at least one acrylic acid monomer,
- a second block with a $T_g$ of greater than or equal to 40° C., for example ranging from 85 to 125° C., which is a homopolymer composed of methyl methacrylate monomers, and
- an intermediate block comprising at least one methyl acrylate or methyl methacrylate monomer, and
- an intermediate block comprising methyl methacrylate, at least one acrylic acid monomer and at least one methyl acrylate monomer.

According to a second variant of this second embodiment, the polymer used in the composition according to the invention may comprise:
- a first block with a $T_g$ of between 20 and 40° C., for example with a $T_g$ of 21 to 39° C., which is a copolymer comprising isobornyl acrylate/isobutyl methacrylate/2-ethylhexyl acrylate,
- a second block with a $T_g$ of less than or equal to 20° C., for example ranging from −65 to −35° C., which is a methyl methacrylate homopolymer, and
- an intermediate block that is an isobornyl acrylate/isobutyl methacrylate/2-ethylhexyl acrylate random copolymer.

According to a third variant of this second embodiment, the polymer used in the composition according to the invention may comprise:
- a first block with a $T_g$ of between 20 and 40° C., for example with a $T_g$ from 21 to 39° C., which is an isobornyl acrylate/methyl acrylate/acrylic acid copolymer,
- a second block with a $T_g$ of greater than or equal to 40° C., for example ranging from 85 to 115° C., which is an isobornyl acrylate homopolymer, and
- an intermediate block that is an isobornyl acrylate/methyl acrylate/acrylic acid random copolymer.

Grafted Ethylenic Polymers Suitable for use as Film-forming Polymers:

The film-forming polymer may also be in the form of a dispersion of particles, preferably solid particles, of a grafted-ethylenic polymer in a liquid fatty phase. Such a dispersion is especially described in the international patent application filed under the filing number PCT/FR03/03709, the entire content of which is hereby incorporated by reference. The term "ethylenic" polymer means a polymer obtained by polymerization of ethylenically unsaturated monomers.

The dispersion of grafted ethylenic polymer is especially free of stabilizing polymer different from the said grafted polymer, such as those described in EP0749747 and described hereinbelow, and the particles of grafted ethylenic polymer are therefore not surface-stabilized with such additional stabilizing polymers. The grafted polymer is therefore dispersed in the liquid fatty phase in the absence of additional surface stabilizer for the particles.

The term "grafted" polymer means a polymer having a skeleton comprising at least one side chain that is pendent or located at the end of a chain, and preferably pendent.

Advantageously, the grafted ethylenic polymer comprises an ethylenic skeleton that is insoluble in the said liquid fatty phase, and side chains covalently bonded to the said skeleton, which are soluble in the liquid fatty phase.

The grafted ethylenic polymer is especially a non-crosslinked polymer. In particular, the polymer is obtained by polymerization of monomers comprising only one polymerizable group.

The grafted ethylenic polymer is preferably a film-forming polymer.

The term "film-forming" polymer means a polymer capable, by itself or in the presence of an auxiliary film-forming agent, of forming a continuous film that adheres to a support, especially to keratin materials, preferably a cohesive film and better still a film whose cohesion and mechanical properties are such that the said film may be isolated from the said support.

According to one embodiment of the invention, the grafted ethylenic polymer is a grafted acrylic polymer.

The grafted ethylenic polymer may especially be obtained by free-radical polymerization in an organic polymerization medium:
- of at least one ethylenic monomer, in particular of at least one acrylic monomer and optionally of at least one additional non-acrylic vinyl monomer, to form the said insoluble skeleton; and
- of at least one macromonomer comprising a polymerizable end group to form the side chains, the said macromonomer having a weight-average molecular mass of greater than or equal to 200 and the content of polymerized macromonomer representing from 0.05% to 20% by weight of the polymer.

The liquid fatty phase may contain the organic polymerization medium for the grafted ethylenic polymer.

The organic liquid dispersion medium, corresponding to the medium in which the grafted polymer is supplied, may be identical to the polymerization medium.

However, the polymerization medium may be totally or partially replaced with another organic liquid medium. This other organic liquid medium may be added, after polymerization, to the polymerization medium. The said polymerization medium is then totally or partially evaporated.

The liquid fatty phase may contain liquid organic compounds other than those present in the dispersion medium. These other compounds are chosen such that the grafted polymer remains in dispersed form in the liquid fatty phase.

The organic liquid dispersion medium is present in the liquid fatty phase of the composition according to the invention due to the introduction into the composition of the dispersion of grafted polymer obtained.

A) Liquid Fatty Phase:

The liquid fatty phase comprises, preferably predominantly, one or more liquid organic compounds (or oils) as defined below.

In particular, the liquid fatty phase is a non-aqueous liquid organic phase that is immiscible with water at room temperature (25° C.).

The term "liquid organic compound" means a non-aqueous compound that is in liquid form at room temperature (25° C.) and therefore flows under its own weight.

The term "silicone compound" means a compound containing at least one silicon atom.

The composition according to the invention advantageously contains a volatile oil as described below.

The term "volatile oil" means an oil capable of evaporating from the skin, the lips or keratin fibers in less than one hour, especially having a vapor pressure, at room temperature and atmospheric pressure, ranging from $10^{-3}$ to 300 mmHg (0.13 Pa to 40,000 Pa).

The volatile oil may be silicone-based or non-silicone-based. It may be chosen especially from octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane, isododecane, isodecane and isohexadecane, and mixtures thereof.

The volatile oil is advantageously present in an amount ranging from 1% to 70% by weight, preferably from 5% to 50% by weight and preferably from 10% to 35% by weight, based on the weight of the composition.

The liquid fatty phase may contain a non-volatile oil as described below.

The non-volatile oil is advantageously present in an amount ranging from 1% to 80% by weight, preferably from 5% to 60% by weight and preferably from 10% to 50% by weight, based on the weight of the composition.

Among the liquid organic compounds or oils that may be present in the liquid organic dispersion medium, mention may be made of:
- liquid organic compounds, especially silicone-based or non-silicone-based, having a global solubility parameter according to the Hansen solubility space of less than or equal to 18 $(MPa)^{1/2}$ and preferably less than or equal to 17 $(MPa)^{1/2}$,
- monoalcohols having a global solubility parameter according to the Hansen solubility space of less than or equal to 20 $(MPa)^{1/2}$, and
- mixtures thereof.

The global solubility parameter δ according to the Hansen solubility space is defined in the article "Solubility parameter values" by Eric A. Grulke in the book "Polymer Handbook", 3rd Edition, Chapter VII, p. 519-559, by the relationship:

$$\delta = (d_D^2 + d_P^2 + d_H^2)^{1/2}$$

in which
- $d_D$ characterizes the London dispersion forces arising from the formation of dipoles induced during molecular impacts,
- $d_P$ characterizes the Debye interaction forces between permanent dipoles, and
- $d_H$ characterizes the forces of specific interactions (such as hydrogen bonding, acid/base, donor/acceptor, etc.).

The definition of solvents in the solubility space according to Hansen is described in the article by C. M. Hansen: "The three-dimensional solubility parameters", J. Paint Technol. 39, 105 (1967).

Among the liquid organic compounds, especially silicone-based or non-silicone-based, having a global solubility parameter according to the Hansen solubility space of less than or equal to 18 $(MPa)^{1/2}$, mention may be made of liquid fatty substances, especially oils, which may be chosen from natural or synthetic, carbon-based, hydrocarbon-based, fluoro and silicone oils, which are optionally branched, alone or as a mixture.

Among these oils, mention may be made of plant oils formed from fatty acid esters and from polyols, in particular triglycerides, such as sunflower oil, sesame oil or rapeseed oil, or esters derived from acids or alcohols containing a long chain (i.e. a chain containing from 6 to 20 carbon atoms), in particular the esters of formula TCOOT' in which T represents a higher fatty acid residue containing from 7 to 19 carbon atoms and T' represents a hydrocarbon-based chain containing from 3 to 20 carbon atoms, such as palmitates, adipates and benzoates, in particular diisopropyl adipate. Mention may also be made of linear, branched and/or cyclic alkanes which may be volatile, and in particular liquid paraffin, liquid petroleum jelly or hydrogenated polyisobutylene, isododecane or "Isopars", volatile isoparaffins. Mention may also be made of esters, ethers and ketones.

Mention may also be made of silicone oils such as polydimethylsiloxanes and polymethylphenylsiloxanes, optionally substituted with aliphatic and/or aromatic groups, which are optionally fluorinated, or with functional groups such as hydroxyl, thiol and/or amine groups, and volatile silicone oils, which are especially cyclic.

In particular, mention may be made of volatile and/or non-volatile, optionally branched silicone oils.

The term "volatile oil" means an oil capable of evaporating from the skin or the lips in less than one hour, and especially having a vapor pressure, at room temperature and atmospheric pressure, ranging from $10^{-3}$ to 300 mmHg (0.13 Pa to 40,000 Pa).

As volatile silicone oils that may be used in the invention, mention may be made of linear or cyclic silicones containing from 2 to 7 silicon atoms, these silicones optionally comprising alkyl or alkoxy groups containing from 1 to 10 carbon atoms. Mention may be made in particular of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof.

Among the non-volatile silicone oils that may be mentioned are non-volatile polydialkylsiloxanes, such as non-volatile polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl trimethyl-siloxy diphenylsiloxanes, diphenyl dimethicones, diphenyl methyldiphenyltrisiloxanes and polymethyl-phenylsiloxanes; polysiloxanes modified with fatty acids (especially of $C_8$-$C_{20}$), fatty alcohols. (especially of $C_8$-$C_{20}$) or polyoxyalkylenes (especially polyoxy-ethylene and/or polyoxypropylene); amino polysiloxanes; polysiloxanes containing hydroxyl groups; fluoro poly-siloxanes comprising a fluorinated group that is pendent or at the end of a silicone chain, containing from 1 to 12 carbon atoms, all or some of the hydrogen atoms of which are replaced with fluorine atoms; and mixtures thereof.

As non-silicone-based liquid organic compounds with a global solubility parameter according to the Hansen solubility space of less than or equal to 18 $(MPa)^{1/2}$, mention may be made in particular of:
  linear, branched or cyclic esters containing at least 6 carbon atoms, especially 6 to 30 carbon atoms;
  ethers containing at least 6 carbon atoms, especially 6 to 30 carbon atoms; and
  ketones containing at least 6 carbon atoms, especially 6 to 30 carbon atoms.

The expression "liquid monoalcohols having a global solubility parameter according to the Hansen solubility space of less than or equal to 20 $(MPa)^{1/2}$" means aliphatic fatty liquid monoalcohols containing 6 to 30 carbon atoms, the hydrocarbon-based chain not comprising a substitution group. Monoalcohols according to the invention that may be mentioned include oleyl alcohol, decanol, octyldodecanol and linoleyl alcohol.

Non-silicone Medium

According to a first embodiment of the invention, the liquid fatty phase may be a non-silicone liquid fatty phase.

The term "non-silicone liquid fatty phase" means a fatty phase comprising one or more non-silicone liquid organic compounds or oils, such as those mentioned above, the said non-silicone compounds being predominantly present in the liquid fatty phase, i.e. to at least 50% by weight, especially from 50% to 100% by weight, preferably from 60% to 100% by weight (for example from 60% to 99% by weight), or alternatively from 65% to 100% by weight (for example from 65% to 95% by weight), relative to the total weight of the liquid fatty phase.

The non-silicone liquid organic compounds may especially be chosen from:
  non-silicone liquid organic compounds with a global solubility parameter according to the Hansen solubility space of less than or equal to 18 $(MPa)^{1/2}$,
  monoalcohols with a global solubility parameter according to the Hansen solubility space of less than or equal to 20 $(MPa)^{1/2}$; and
  mixtures thereof.

The non-silicone liquid fatty phase may thus optionally comprise silicone liquid organic compounds or oils, such as those mentioned previously, which may be present in an amount of less than 50% by weight, especially ranging from 0.1% to 40% by weight, or even ranging from 1% to 35% by weight, or alternatively ranging from 5% to 30% by weight, relative to the total weight of the liquid fatty phase.

According to one particular embodiment of the invention, the non-silicone liquid fatty phase does not contain any silicone liquid organic compounds or oils.

When the liquid fatty phase is a non-silicone liquid fatty phase, the macromonomers present in the grafted polymer are advantageously carbon-based macromonomers as described below.

In particular, when the liquid fatty phase is a non-silicone liquid fatty phase, the grafted polymer present in the composition is advantageously a non-silicone grafted polymer.

The term "non-silicone grafted polymer" means a grafted polymer predominantly containing a carbon-based macromonomer and optionally containing not more than 7% by weight and preferably not more than 5% by weight of silicone macromonomer, or even being free of silicone macromonomer.

Silicone-based Medium:

According to a second embodiment of the invention, the liquid fatty phase may be a silicone-based liquid fatty phase.

The term "silicone-based liquid fatty phase" means a fatty phase comprising one or more silicone-based liquid organic compounds or silicone oils such as those described previously, the said silicone compounds being predominantly present in the liquid fatty phase, i.e. to at least 50% by weight, especially from 50% to 100% by weight, preferably from 60% to 100% by weight (for example from 60% to 99% by weight), or even from 65% to 100% by weight (for example from 65% to 95% by weight), relative to the total weight of the liquid fatty phase.

The silicone-based liquid organic compounds may especially be chosen from:
  liquid organic compounds, which are especially non-silicone-based or silicone-based, with an overall solubility parameter according to the Hansen solubility space of less than or equal to 18 $(MPa)^{1/2}$.

The silicone-based liquid fatty phase may thus optionally comprise non-silicone-based liquid organic compounds or oils, as described previously, which may be present in an amount of less than 50% by weight, especially ranging from 0.1% to 40% by weight, or even ranging from 1% to 35% by weight, or else ranging from 5% to 30% by weight, relative to the total weight of the liquid fatty phase.

According to one particular embodiment of the invention, the silicone-based liquid fatty phase does not contain any non-silicone-based liquid organic compounds.

When the liquid fatty phase is a silicone-based liquid fatty phase, the macromonomers present in the grafted polymer are advantageously silicone-based macromonomers as described below.

In particular, when the liquid fatty phase is-a silicone-based liquid fatty phase, the grafted polymer present in the composition is advantageously a silicone-based grafted polymer.

The term "silicone-based grafted polymer" means a grafted polymer predominantly containing a silicone-based macromonomer and optionally containing up to 7% by weight and preferably up to 5% by weight of carbon-based macromonomer, or even being free of carbon-based macromonomer.

B) Grafted Ethylenic Polymer

In order to obtain a dispersion of particles of grafted ethylenic polymer and, specifically, a stable dispersion thereof, numerous variables and their interreaction with the liquid organic dispersion medium must be taken into account by those skilled in the art. The variables include, but are not limited to, the choice of monomers and macromonomers constituting the skeleton of the grafted ethylenic polymer, the molecular weight of the grafted ethylenic polymer and the proportion of monomers and macromonomers used to make the grafted ethylenic polymer.

The term "stable dispersion" means a dispersion that is not liable to form a solid deposit or to undergo liquid/solid phase separation, especially after centrifugation, for example at 4,000 rpm for 15 minutes.

The grafted ethylenic polymer forming the particles in dispersion thus comprises a skeleton that is insoluble in the said dispersion medium and a portion that is soluble in the said dispersion medium.

The grafted ethylenic polymer may be a random polymer.

According to the invention, the term "grafted ethylenic polymer" means a polymer that may be obtained by free-radical polymerization:
 of one or more ethylenic monomer(s);
 with one or more macromonomer(s), in an organic polymerization medium.

According to the invention, the term "grafted acrylic polymer" means a polymer that may be obtained by free-radical polymerization:
 of one or more acrylic monomer(s), and optionally of one or more additional non-acrylic vinyl monomer(s);
 with one or more macromonomer(s), in an organic polymerization medium.

Advantageously, the acrylic monomers represent from 50% to 100% by weight, preferably from 55% to 100% by weight (especially from 55% to 95% by weight) and preferably from 60% to 100% by weight (especially from 60% to 90% by weight) of the mixture of acrylic monomers+ optional non-acrylic vinyl monomers.

Preferably, the acrylic monomers are chosen from monomers whose homopolymer is insoluble in the dispersion medium under consideration, i.e. the homopolymer is in solid (or non-dissolved) form at a concentration of greater than or equal to 5% by weight at room temperature (20° C.) in the said dispersion medium.

a) Macromonomers:

According to the invention, the expression "macromonomer containing a polymerizable end group" means any polymer comprising on only one of its ends a polymerizable end group capable of reacting during the polymerization reaction with acrylic monomers and optionally the additional non-acrylic vinyl monomers constituting the skeleton. The macromonomer makes it possible to form the side chains of the grafted acrylic polymer. The polymerizable group of the macromonomer may advantageously be an ethylenically unsaturated group capable of free-radical polymerization with the monomers constituting the skeleton.

The term "carbon-based macromonomer" means a non-silicone-based macromonomer and especially an oligomeric macromonomer obtained by polymerization of ethylenically unsaturated non-silicone-based monomer(s), and mainly by polymerization of acrylic and/or non-acrylic vinyl monomers.

The term "silicone-based macromonomer" means an organopolysiloxane macromonomer and in particular a polydimethylsiloxane macromonomer.

Preferably, the macromonomer is chosen from macromonomers whose homopolymer is soluble in the dispersion medium under consideration, i.e. fully dissolved at a concentration of greater than or equal to 5% by weight and at room temperature in the said dispersion medium.

Thus, the grafted acrylic polymer comprises a skeleton (or main chain) consisting of a sequence of acrylic units resulting from the polymerization especially of one or more acrylic monomers and of side chains (or grafts) derived from the reaction of the macromonomers, the said side chains being covalently bonded to the said main chain.

The skeleton (or main chain) is insoluble in the dispersion medium under consideration, whereas the side chains (or grafts) are soluble in the said dispersion medium.

b) Monomers:

In the present patent application, the term "acrylic monomers" means monomers chosen from (meth)-acrylic acid, (meth)acrylic acid esters (also known as (meth)acrylates), and (meth)acrylic acid amides (also known as (meth)acrylamides).

As acrylic monomers that may be used to constitute the insoluble skeleton of the polymer, mention may be made, alone or as a mixture, of the following monomers, and also the salts thereof:
 (i) the (meth)acrylates of formula:

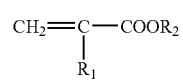

in which:
 $R_1$ denotes a hydrogen atom or a methyl group;
 $R_2$ represents a group chosen from:
  a linear or branched alkyl group containing from 1 to 6 carbon atoms, the said group possibly comprising in its chain one or more hetero atoms chosen from O, N and S; and/or possibly comprising one or more substituents chosen from —OH, halogen atoms (F, Cl, Br or I) and —NT$_1$T$_2$ with T$_1$ and T$_2$, which may be identical or different, chosen from linear or branched C$_1$-C$_4$ alkyls; and/or possibly being substituted with at least one polyoxyalkylene group, in particular with C$_2$-C$_4$ alkylene, especially polyoxyethylene and/or polyoxypropylene, the said polyoxyalkylene group consisting of a repetition of 5 to 30 oxyalkylene units;

a cyclic alkyl group containing from 3 to 6 carbon atoms, the said group possibly comprising in its chain one or more hetero atoms chosen from O, N and S, and/or possibly comprising one or more substituents chosen from OH and halogen atoms (F, Cl, Br or I).

Examples of R$_2$ that may be mentioned include the methyl, ethyl, propyl, butyl, isobutyl, methoxyethyl, ethoxyethyl, methoxypolyoxyethylene (350 OE), trifluoroethyl, 2-hydroxyethyl, 2-hydroxypropyl, dimethylaminoethyl, diethylaminoethyl or dimethylaminopropyl group;

(ii) the (meth)acrylamides of formula:

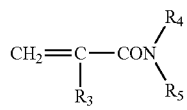

in which:
R$_3$ denotes a hydrogen atom or a methyl group;

R$_4$ and R$_5$, which may be identical or different, represent a hydrogen atom or a linear or branched alkyl group containing from 1 to 6 carbon atoms, which may comprise one or more substituents chosen from —OH, halogen atoms (F, Cl, Br or I) and —NR'R" with R' and R", which may be identical or different, chosen from linear or branched C$_1$-C$_4$ alkyls; or R$_4$ represents a hydrogen atom and R$_5$ represents a 1,1-dimethyl-3-oxobutyl group.

As examples of alkyl groups that can constitute R$_4$ and R$_5$, mention may be made of n-butyl, t-butyl, n-propyl, dimethylaminoethyl, diethylaminoethyl and dimethylaminopropyl;

(iii) (meth)acrylic monomers comprising at least one carboxylic acid, phosphoric acid or sulfonic acid function, such as acrylic acid, methacrylic acid or acrylamidopropanesulfonic acid.

Among these acrylic monomers, those that may be mentioned most particularly are methyl, ethyl, propyl, butyl and isobutyl(meth)acrylates; methoxyethyl or ethoxyethyl (meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate, 2-hydroxyethyl acrylate; dimethylaminopropylmethacrylamide; and the salts thereof; and mixtures thereof.

Preferably, the acrylic monomers are chosen from methyl acrylate, methoxyethyl acrylate, methyl methacrylate, 2-hydroxyethyl methacrylate, acrylic acid and dimethylaminoethyl methacrylate, and mixtures thereof.

Among the additional non-acrylic vinyl monomers that may be mentioned are:

vinyl esters of formula: R$_6$—COO—CH═CH$_2$
in which R$_6$ represents a linear or branched alkyl group containing from 1 to 6 atoms, or a cyclic alkyl group containing from 3 to 6 carbon atoms and/or an aromatic group, for example of benzene, anthracene or naphthalene type;

non-acrylic vinyl monomers comprising at least one carboxylic acid, phosphoric acid or sulfonic acid function, such as crotonic acid, maleic anhydride, itaconic acid, fumaric acid, maleic acid, styrenesulfonic acid, vinylbenzoic acid or vinylphosphoric acid, and the salts thereof;

non-acrylic vinyl monomers comprising at least one tertiary amine function, such as 2-vinylpyridine or 4-vinylpyridine;

and mixtures thereof.

Advantageously, the acrylic monomers present in the grafted polymer comprise at least (meth)acrylic acid and at least one monomer chosen from the (meth)acrylates and (meth)acrylamides described previously in points (i) and (ii). Preferably, the acrylic monomers comprise at least (meth)acrylic acid and at least one monomer chosen from C$_1$-C$_3$ alkyl (meth)acrylates. (Meth)acrylic acid may be present in an amount of at least 5% by weight, especially from 5% to 80% by weight, preferably of at least 10% by weight, especially from 10% to 70% by weight, and preferably of at least 15% by weight, especially from 15% to 60% by weight, relative to the total weight of the polymer.

Among the salts that may be mentioned are those obtained by neutralization of acid groups with mineral bases such as sodium hydroxide, potassium hydroxide or ammonium hydroxide, or organic bases such as alkanolamines, for instance monoethanolamine, diethanolamine, triethanolamine or 2-methyl-2-amino-1-propanol.

Mention may also be made of the salts formed by neutralization of tertiary amine units, for example using a mineral or organic acid. Among the mineral acids that may be mentioned are sulfuric acid, hydrochloric acid, hydrobromic acid, hydriodic acid, phosphoric acid and boric acid. Among the organic acids that may be mentioned are acids comprising one or more carboxylic, sulfonic or phosphonic groups. They may be linear, branched or cyclic aliphatic acids, or alternatively aromatic acids. These acids may also comprise one or more hetero atoms chosen from O and N, for example in the form of hydroxyl groups. Acetic acid or propionic acid, terephthalic acid, and citric acid and tartaric acid may especially be mentioned.

According to one embodiment of the invention, the grafted ethylenic polymer contains no additional non-acrylic vinyl monomers as described above. In this embodiment, the insoluble skeleton of the grafted ethylenic polymer is formed solely from acrylic monomers as described previously.

It is understood that these non-polymerized acrylic monomers may be soluble in the dispersion medium under consideration, but the polymer formed with these monomers is insoluble in the dispersion medium.

According to one particular embodiment of the invention, the grafted ethylenic polymer may be obtained by free-radical polymerization in an organic polymerization medium:

of a main acrylic monomer chosen from C$_1$-C$_3$ alkyl (meth)acrylates, alone or as a mixture, and optionally of one or more additional acrylic monomers chosen from (meth)acrylic acid, methacrylic acid and alkyl (meth)acrylates of formula (I) defined below, and salts thereof, to form the said insoluble skeleton; and of at least one silicone-based macromonomer comprising a polymerizable end group, as defined previously.

Main acrylic monomers that may be used include methyl acrylate, methyl methacrylate, ethyl acrylate, ethyl methacrylate, n-propyl acrylate, n-propyl methacrylate, isopropyl acrylate and isopropyl methacrylate, and mixtures thereof.

Methyl acrylate, methyl methacrylate and ethyl methacrylate are most particularly preferred.

The additional acrylic monomers may be chosen from:
(meth)acrylic acid and its salts,
the (meth)acrylates of formula (I), and salts thereof:

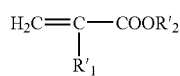
(I)

in which:
$R'_1$ denotes a hydrogen atom or a methyl group;
$R'_2$ represents
a linear or branched alkyl group containing from 1 to 6 carbon atoms, the said group comprising in its chain one or more oxygen atoms and/or comprising one or more substituents chosen from
OH, halogen atoms (F, Cl, Br or I) and —NR'R", with R' and R", which may be identical or different, being chosen from linear or branched $C_1$-$C_3$ alkyls;
a cyclic alkyl group containing from 3 to 6 carbon atoms, the said group possibly comprising in its chain one or more oxygen atoms and/or possibly comprising one or more substituents chosen from OH and halogen atoms (F, Cl, Br or I);
and mixtures thereof.

Examples of $R'_2$ that may be mentioned include the methoxyethyl, ethoxyethyl, trifluoroethyl, 2-hydroxyethyl, 2-hydroxypropyl, dimethylaminoethyl, diethylaminoethyl and dimethylaminopropyl groups.

Among these additional acrylic monomers, mention may be made most particularly of (meth)-acrylic acid, methoxyethyl or ethoxyethyl(meth)acrylates; trifluoroethyl methacrylate; dimethylaminoethyl methacrylate, diethylaminoethyl methacrylate, 2-hydroxy-propyl methacrylate, 2-hydroxyethyl methacrylate, 2-hydroxypropyl acrylate and 2-hydroxy-ethyl acrylate, the salts thereof, and mixtures thereof.

Acrylic acid and methacrylic acid are most particularly preferred.

The macromonomers comprise at one of the ends of the chain a polymerizable end group capable of reacting during the polymerization with the acrylic monomers and optionally the additional vinyl monomers, to form the side chains of the grafted ethylenic polymer. The said polymerizable end group may in particular be a vinyl or (meth)acrylate (or (meth)-acryloxy) group, and preferably a (meth)acrylate group.

The macromonomers are preferably chosen from macromonomers whose homopolymer has a glass transition temperature ($T_g$) of less than or equal to 25° C., especially ranging from −100° C. to 25° C. and preferably ranging from −80° C. to 0° C.

The macromonomers have a weight-average molecular mass of greater than or equal to 200, preferably greater than or equal to 300, preferably greater than or equal to 500 and more preferably greater than 600.

Preferably, the macromonomers have a weight-average molecular mass (Mw) ranging from 200 to 100,000, preferably ranging from 500 to 50,000, preferably ranging from 800 to 20,000, more preferably ranging from 800 to 10,000 and even more preferably ranging from 800 to 6,000.

In the present patent application, the weight-average (Mw) and number-average (Mn) molar masses are determined by liquid gel permeation chromatography (THF solvent, calibration curve established with linear polystyrene standards, refractometric detector).

Carbon-based macromonomers that may in particular be mentioned include:
(i) homopolymers and copolymers of linear or branched $C_8$-$C_{22}$ alkyl acrylate or methacrylate, containing a polymerizable end group chosen from vinyl or (meth)acrylate groups, among which mention may be made in particular of: poly(2-ethylhexyl acrylate) macromonomers with a mono(meth)acrylate end group; poly(dodecyl acrylate) or poly(dodecyl methacrylate) macromonomers with a mono(meth)acrylate end group; poly(stearyl acrylate) or poly(stearyl methacrylate) macromonomers with a mono(meth)acrylate end group.

Such macromonomers are described in particular in the patents EP 895467 and EP 96459, and in the article by Gillman K. F., Polymer Letters, Vol 5, page 477-481 (1967), the entire contents of which are hereby incorporated by reference.

Mention may be made in particular of macromonomers based on poly(2-ethylhexyl acrylate) or poly(dodecyl acrylate) with a mono(meth)acrylate end group;
(ii) polyolefins containing an ethylenically unsaturated end group, in particular containing a (meth)acrylate end group. Examples of such polyolefins that may be mentioned in particular include the following macromonomers, it being understood that they have a (meth)acrylate end group: polyethylene macromonomers, polypropylene macromonomers, macromonomers of polyethylene/polypropylene copolymer, macromonomers of polyethylene/polybutylene copolymer, polyisobutylene macromonomers; polybutadiene macromonomers; polyisoprene macromonomers; polybutadiene macromonomers; poly(ethylene/butylene)-polyisoprene macromonomers.

Such macromonomers are described in particular in U.S. Pat. No. 5,625,005, the entire content of which is hereby incorporated by reference, which mentions ethylene/butylene and ethylene/propylene macromonomers containing a (meth)acrylate reactive end group.

Mention may be made in particular of the poly(ethylene/butylene)methacrylate such as that sold under the name Kraton Liquid L-1253 by Kraton Polymers.

Silicone-based macromonomers that may be mentioned in particular include polydimethylsiloxanes containing mono (meth)acrylate end groups, and especially those of formula (II) below:

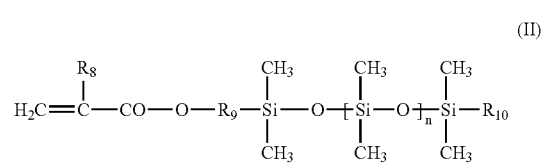
(II)

in which $R_8$ denotes a hydrogen atom or a methyl group; $R_9$ denotes a divalent hydrocarbon-based group containing from 1 to 10 carbon atoms and optionally contains one or two ether bonds —O—; $R_{10}$ denotes an alkyl group containing from 1 to 10 carbon atoms and especially from 2 to 8 carbon atoms; n denotes an integer ranging from 1 to 300, preferably ranging from 3 to 200 and preferably ranging from 5 to 100.

Silicone-based macromonomers that may be used include monomethacryloxypropyl polydimethylsiloxanes such as those sold under the name PS560-K6 by the company United Chemical Technologies Inc. (UCT) or under the name MCR-M17 by the company Gelest Inc.

Preferably, the polymerized macromonomer (constituting the side chains of the grafted polymer) represents from 0.1% to 15% by weight, preferably from 0.2% to 10% by weight and more preferably from 0.3% to 8% by weight, relative to the total weight of the polymer.

As particularly preferred grafted ethylenic polymer dispersed in a non-silicone liquid fatty phase, it is possible to use those obtained by polymerization:

of methyl acrylate and of a polyethylene/polybutylene macromonomer containing a methacrylate end group (especially Kraton L-1253), in particular in a solvent chosen from isododecane, isononyl isononanoate, octyldodecanol, diisostearyl malate or a $C_{12}$-$C_{15}$ alkyl benzoate (such as Finsolv TN);

of methoxyethyl acrylate and of a polyethylene/polybutylene macromonomer containing a methacrylate end group (especially Kraton L-1253), in particular in isododecane;

of methyl acrylate/methyl methacrylate monomers and of a polyethylene/polybutylene macromonomer containing a methacrylate end group (especially Kraton L-1253), in particular in isododecane;

of methyl acrylate/acrylic acidic monomers and of a polyethylene/polybutylene macromonomer containing a methacrylate end group (especially Kraton L-1253), in particular in isododecane;

of methyl acrylate/dimethylaminoethyl methacrylate monomers and of a polyethylene/polybutylene macromonomer containing a methacrylate end group (especially Kraton L-1253), in particular in isododecane;

of methyl acrylate/2-hydroxyethyl methacrylate monomers and of a polyethylene/polybutylene macromonomer containing a methacrylate end group (especially Kraton L-1253), in particular in isododecane.

As particularly preferred grafted acrylic polymer dispersed in a silicone-based liquid fatty phase, it is possible to use those obtained by polymerization:

of methyl acrylate and of the monomethacryloyloxypropyl polydimethylsiloxane macromonomer with a weight-average molecular weight ranging from 800 to 6,000, in particular in decamethylcyclopentasiloxane or phenyl trimethicone;

of methyl acrylate, acrylic acid and the monomethacryloxypropyl polydimethylsiloxane macromonomer with a weight-average molecular weight ranging from 800 to 6,000, in particular in decamethylcyclopentasiloxane or phenyl trimethicone.

The weight-average molecular mass (Mw) of the grafted polymer is preferably between 10,000 and 300,000, especially between 20,000 and 200,000 and better still between 25,000 and 150,000.

By virtue of the abovementioned characteristics, in a given organic dispersion medium, the polymers have the capacity of folding over on themselves, thus forming particles of substantially spherical shape, the periphery of these particles having the deployed side chains, which ensure the stability of these particles. Such particles resulting from characteristics of the grafted polymer have the particular feature of not aggregating in the said medium and thus of being self-stabilized and of forming a particularly stable polymer particle dispersion.

In particular, the grafted ethylenic polymers of the dispersion are capable of forming nanometer-sized particles, with a mean size ranging from 10 to 400 nm and preferably from 20 to 200 nm.

As a result of this very small size, the grafted polymer particles in dispersion are particularly stable and therefore have little susceptibility to form aggregates.

The dispersion of grafted polymer may thus be a dispersion that is stable and does not form sediments when it is placed at room temperature for an extended period (for example 24 hours).

Preferably, the dispersion of grafted polymer particles has a solids content (or dry extract) of polymer of from 40% to 70% by weight of solids and especially from 45% to 65% by weight.

The dispersion of grafted polymer particles may be prepared via a process comprising a step free-radical copolymerization, in an organic polymerization medium, of one or more acrylic monomers as defined above with one or more macromonomers as defined above.

As mentioned previously, the liquid organic dispersion medium may be identical to or different from the polymerization medium.

The copolymerization may be performed conventionally in the presence of a polymerization initiator. The polymerization initiators may be free-radical initiators. In general, such a polymerization initiator may be chosen from organic peroxide compounds such as dilauroyl peroxide, dibenzoyl peroxide or tert-butyl peroxy-2-ethylhexanoate; diazo compounds such as azobisisobutyronitrile or azobisdimethylvaleronitrile.

The reaction may also be initiated using photoinitiators or with radiation such as UV or neutrons, or with plasma.

In general, to perform this process, at least a portion of the organic polymerization medium, a portion of the additional acrylic and/or vinyl monomers, which will constitute the insoluble skeleton after polymerization, all of the macromonomer (which will constitute the side chains of the polymer) and a portion of the polymerization initiator are introduced into a reactor whose size is suitable for the amount of polymer to be prepared. At this stage of introduction, the reaction medium forms a relatively homogeneous medium.

The reaction medium is then stirred and heated up to a temperature to obtain polymerization of the monomers and macromonomers. After a certain time, the initially homogeneous and clear medium leads to a dispersion of milky appearance. A mixture consisting of the remaining portion of monomers and of polymerization initiator is then added. After an adequate time during which the mixture is heated with stirring, the medium stabilizes in the form of a milky dispersion, the dispersion comprising polymer particles stabilized in the medium in which they have been created, the said stabilization being due to the presence, in the polymer, of side chains that are soluble in the said dispersion medium.

Structuring Agents:

The term "structuring agent" means a compound capable of increasing the viscosity of the composition. The structuring agent makes it possible especially to obtain a composition that can have a texture ranging from fluid to solid textures.

Examples of suitable structuring agents include, but are not limited to, thickeners (aqueous-medium thickeners; oily-medium thickeners), organogelling agents, waxes, pasty compounds and gums.

Suitable aqueous-medium thickeners include, but are not limited to:
- hydrophilic clays,
- hydrophilic fumed silica,
- water-soluble cellulose-based thickeners,
- carob gum, scleroglucan gum, gellan gum, or rhamsan gum,
- maltodextrins, starch and their derivatives,
- polyglyceryl(meth)acrylate polymers sold under the names "Hispagel" or "Lubragel" by the companies Hispano Qimica or Guardian,
- crosslinked acrylamide polymers and copolymers, such as those sold under the names "PAS 5161" or "Bozepol C" by the company Hoechst, "Sepigel 305" by the company SEPPIC,
- crosslinked methacryloyloxyethyltrimethylammonium chloride homopolymers sold under the name "Salcare SC95" by the company Allied Colloid,
- associative polymers and especially associative polyurethanes.

Such thickeners are described especially in patent application EP1400234 A, the entire content of which is hereby incorporated by reference.

Suitable oily-medium thickeners include, but are not limited to:
- organophilic clays;
- hydrophobic fumed silicas;
- alkyl guar gums (with a $C_1$-$C_6$ alkyl group), such as those described in EP0708114 A, the entire content of which is hereby incorporated by reference,
- polymers having a weight-average molecular mass of less than 100,000, comprising: a) a polymer skeleton containing hydrocarbon-based repeating units containing at least one hetero atom and, optionally, b) at least one pendent fatty chain and/or at least one terminal fatty chain, which are optionally functionalized, containing from 6 to 120 carbon atoms and being linked to these hydrocarbon-based units, as described in patent applications WO02/056847 and WO02/47619, the entire contents of which are hereby incorporated by reference; in particular, polyamide resins (especially comprising alkyl groups containing from 12 to 22 carbon atoms) such as those described in U.S. Pat. No. 5,783,657, the entire content of which is hereby incorporated by reference;
- the silicone-based polyamide resins as described in patent application EP1266647 A and in the French patent application filed under the number 0216039, the entire contents of which are hereby incorporated by reference.

Such thickeners are especially described in patent application EP1400234 A, the entire contents of which is hereby incorporated by reference.

The organogelling agents may be chosen from those described in patent application WO03/105788, the entire content of which is hereby incorporated by reference.

The organogelling agents that may be used in the composition disclosed herein may be, for example, chosen from those described in the document "Specialist Surfactants" edited by D. Robb, 1997, pp. 209-263, Chapter 8 by P. Terech, European patent applications EP-A-1 068 854 and EP-A-1 086 945, or alternatively in patent application WO-A-02/47031, the entire contents of which are hereby incorporated by reference.

Mention may be made, for example, among these organogelling agents, of amides of carboxylic acids, such as tricarboxylic acids, for instance cyclohexanetricarboxamides (see European patent application EP-A-1 068 854 the entire content of which is hereby incorporated by reference), diamides with hydrocarbon-based chains each comprising from 1 to 22 carbon atoms, for example from 6 to 18 carbon atoms, wherein the hydrocarbon-based chains may be unsubstituted or substituted with at least one substituent chosen from ester, urea and fluoro groups (see patent application EP-A-1 086 945 the entire contents of which is hereby incorporated by reference) and, for example, diamides resulting from the reaction of diaminocyclohexane, such as diaminocyclohexane in trans form, and of an acid chloride, for instance N,N'-bis(dodecanoyl)-1,2-diaminocyclohexane, N-acylamino acid amides, for instance the diamides resulting from the action of an N-acylamino acid with amines comprising from 1 to 22 carbon atoms, for instance those described in document WO-93/23008 the entire contents of which is hereby incorporated by reference and such as N-acylglutamic acid amides in which the acyl group is a $C_8$ to $C_{22}$ alkyl chain, such as N-lauroyl-L-glutamic acid dibutylamide, manufactured or sold by the company Ajinomoto under the name GP-1, and mixtures thereof.

Structuring agents may also include waxes. The term "wax" means a lipophilic compound, which is solid at room temperature (25° C.), with a reversible solid/liquid change of state, having a melting point of greater than or equal to 30° C., which may be up to 120° C. By bringing the wax to the liquid state (melting), it is possible to render it miscible with any oils present and to form a microscopically homogeneous mixture, but on returning the temperature of the mixture to room temperature, recrystallization of the wax in the oils of the mixture is obtained. The melting point of the wax may be measured using a differential scanning calorimeter (DSC), for example the calorimeter sold under the name DSC 30 by the company Mettler.

The wax may also have a hardness ranging from 0.05 MPa to 15 MPa and preferably ranging from 6 MPa to 15 MPa. The hardness is determined by measuring the compressive force, measured at 20° C. using a texturometer sold under the name TA-TX2i by the company Rheo, equipped with a stainless-steel cylinder 2 mm in diameter, traveling at a measuring speed of 0.1 mm/s, and penetrating into the wax to a penetration depth of 0.3 mm.

Examples of suitable waxes include, but are not limited to, hydrocarbon-based waxes, fluoro waxes and/or silicone waxes and may be of plant, mineral, animal and/or synthetic origin. In particular, the waxes have a melting point of greater than 30° C. and better still greater than 45° C. As waxes that may be used in the composition of the invention, mention may be made of beeswax, carnauba wax or candelilla wax, paraffin, microcrystalline waxes, ceresin or ozokerite; synthetic waxes, for instance polyethylene wax or Fischer-Tropsch wax, silicone waxes, for instance alkyl or alkoxy dimethicone containing from 16 to 45 carbon atoms.

Gums may also be used as viscosifying agents. These gums may be high molecular weight polydimethylsiloxanes (PDMS) or cellulose gums or polysaccharides, and the pasty substances are generally hydrocarbon-based compounds, for instance lanolins and derivatives thereof, or PDMSs.

The viscosifying agents may be present in the composition of the present invention in an amount of from 0.1% to 60% by weight, preferably from 0.1.% to 50% by weight, preferably from 0.5% to 40% by weight, preferably from 0.5% to 30% by weight, more preferably from 0.5% to 20% by weight, and most preferably from 0.5% to 10% by weight, based on the weight of the composition Sunscreens:

The composition according to the invention may comprise a photoprotective system capable of screening out UV radiation.

According to the invention, the photoprotective system may consist of one or more organic screening agents and/or one or more mineral (nano)pigments.

The organic screening agents are chosen especially from anthranilates; cinnamic derivatives; dibenzoylmethane derivatives; salicylic derivatives; camphor derivatives; triazine derivatives such as those described in patent U.S. Pat. No. 4,367,390, and patent applications EP0863145 A, EP0517104 A, EP0570838 A, EP0796851 A, EP0775698 A, EP0878469 A, EP0933376 A, EP0507691 A, EP0507692 A, EP0790243 A, EP0944624 A; benzophenone derivatives; β,β-diphenylacrylate derivatives; benzotriazole derivatives; benzalmalonate derivatives; benzimidazole derivatives; imidazolines; bis-benzazolyl derivatives as described in patents EP0669323 A and U.S. Pat. No. 2,463,264; p-aminobenzoic acid (PABA) derivatives; methylenebis(hydroxyphenylbenzotriazole) derivatives as described in patents or patent applications U.S. Pat. No. 5,237,071, U.S. Pat. No. 5,166, 355, GB 2,303,549,. DE 197 26 184 and EP 0893119 A; screening polymers and screening silicones such as those described especially in patent application WO93/04665; dimers derived from α-alkylstyrene, such as those described in patent application DE 198 55 649; 4,4-diarylbutadienes such as those described in patent applications EP 0967200 A, DE 197 46 654, DE 197 55 649, EP 1008586 A, EP 1133980 A and E P1133981 A, and mixtures thereof.

As examples of UV-A-active and/or UV-B-active organic screening agents, mention may be made of those denoted hereinbelow under their INCI name:

Para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Dibenzoylmethane Derivatives:
Butyl methoxydibenzoylmethane sold in particular under the trade name "Parsol 1789" by Hoffmann LaRoche,
Isopropyldibenzoylmethane.

Cinnamic Derivatives:
Ethylhexyl methoxycinnamate sold in particular under the trade name "Parsol MCX" by Hoffmann LaRoche,
Isopropyl methoxycinnamate,
Isoamyl methoxycinnamate sold under the trade name "Neo Heliopan E 1000" by Haarmann and Reimer,
Cinoxate,
DEA methoxycinnamate,
Diisopropyl methylcinnamate,
Glyceryl ethylhexanoate dimethoxycinnamate.

β,β-Diphenylacrylate Derivatives:
Octocrylene sold in particular under the trade name "Uvinul N539" by BASF,
Etocrylene sold in particular under the trade name "Uvinul N35" by BASF.

Benzophenone Derivatives:
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF,
Benzophenone-12,
n-Hexyl 2-(4-diethylamino-2-hydroxybenzoyl)benzoate.

Benzylidenecamphor Derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Benzimidazole Derivatives:
Phenylbenzimidazolesulfonic acid sold in particular under the trade name "Eusolex 232" by Merck,
Disodium phenyl dibenzimidazole tetrasulfonate sold under the trade name "Neo Heliopan AP" by Haarmann and Reimer.

Triazine Derivatives:
Anisotriazine sold under the trade name "Tinosorb S" by Ciba Specialty Chemicals,
Ethylhexyltriazone sold in particular under the trade name "Uvinul T 150" by BASF,
Diethylhexylbutamidotriazone sold under the trade name "Uvasorb HEB" by Sigma 3V.
2,4,6-Tris(diisobutyl 4'-aminobenzalmalonate)-s-triazine.

Benzotriazole Derivatives:
Drometrizole trisiloxane sold under the name "Silatrizole" by Rhodia Chimie,
Methylenebis(benzotriazolyl)tetramethylbutylphenol sold in solid form under the trade name "Mixxim BB/100" by Fairmount Chemical, or in micronized form as an aqueous dispersion under the trade name "Tinosorb M" by Ciba Specialty Chemicals.

Anthranilic Derivatives:
Menthyl anthranilate sold under the trade name "Neo Heliopan MA" by Haarmann and Reimer.

Imidazoline Derivatives:
Ethylhexyldimethoxybenzylidenedioxoimidazoline propionate.

Benzalmalonate Derivatives:
Polyorganosiloxane containing benzalmalonate functions sold under the trade name "Parsol SLX" by Hoffmann LaRoche 4,4-Diarylbutadiene Derivatives:
1,1-Dicarboxy(2,2'-dimethylpropyl)-4,4-diphenylbutadiene and mixtures thereof.

The organic screening agents that are more particularly preferred are chosen from the following compounds:
Ethylhexyl salicylate,
Ethylhexyl methoxycinnamate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
2,4,6-Tris(diisobutyl 4'-aminobenzalmalonate)-s-triazine,
Anisotriazine,
Ethylhexyltriazone,
Diethylhexylbutamidotriazone,
Methylenebis(benzotriazolyl)tetramethylbutylphenol,
Drometrizole trisiloxane,
1,1-Dicarboxy(2,2'-dimethylpropyl)-4,4-diphenylbutadiene, and mixtures thereof.

The mineral screening agents are chosen from pigments or even nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminum stearate. Such coated or uncoated metal oxide nanopigments are described in particular in patent applications EP0518772 A and EP0518773 A.

The photoprotective system may be present in the composition in an amount of from 0.1% to 30% by weight, preferably from 0.5% to 20% by weight and preferably from 0.5% to 15% by weight, based on the total weight of the composition.

Fibers:

The composition may also contain fibers.

The term "fiber" should be understood as meaning an object of length L and of diameter D such that L is greater than D and preferably very much greater than D, D being the diameter of the circle within which the cross section of the fiber is inscribed. In particular, the ratio L/D (or shape factor) is chosen in the range from 3.5 to 2500, preferably from 5 to 500 and better still from 5 to 150.

Examples of fibers that may be used in the composition of the invention include, but are not limited to, those of synthetic, natural, mineral or organic origin. They may be short or long, individual or organized, for example braided, hollow or solid. They may have any shape and may especially have a circular or polygonal (square, hexagonal or octagonal) cross section depending on the intended specific application. In particular, their ends are blunted and/or polished to prevent injury.

In particular, those fibers having a length ranging from 1 µm to 10 mm, preferably from 0.1 mm to 5 mm and better still from 0.3 mm to 3 mm, are used. Their cross section may be within a circle of diameter ranging from 2 nm to 500 µm, preferably ranging from 100 nm to 100 µm and better still from 1 µm to 50 µm. The weight or yarn count of the fibers is often given in denier or decitex and represents the weight in grams per 9 km of yarn. The fibers according to the invention preferably have a yarn count chosen in the range of from 0.01 to 10 denier, preferably from 0.1 to 2 denier, and more preferably from 0.3 to 0.7 denier.

Examples of suitable fibers include, but are not limited to, those described in the French patent application filed under the number 0450074 and patent applications FR2844710 A and EP1201221 A, the entire contents of which are hereby incorporated by reference.

The fibers may be present in the composition in an amount of from 0.1% to 30% by weight, preferably from 0.1% to 20% by weight and more preferably from 0.1% to 10% by weight, based on the weight of the composition.

Oils:

The composition according to the invention may also comprise at least one oil.

The oil may be chosen from hydrocarbon-based oils, silicone oils and fluoro oils.

The oil may be chosen from volatile oils and non-volatile oils, and mixtures thereof.

The term "hydrocarbon-based oil" means an oil formed essentially from, or even consisting of, carbon and hydrogen atoms, and possibly oxygen or nitrogen atoms, and containing no silicon or fluorine atoms; it may contain ester, ether, amine or amide groups.

The term "silicone oil" means an oil containing at least one silicon atom and especially containing Si—O groups.

The term "fluoro oil" means an oil containing at least one fluorine atom.

The composition according to the invention may comprise at least one volatile oil.

The term "volatile oil" means an oil (or a non-aqueous medium) that can evaporate on contact with the skin in less than one hour, at room temperature and atmospheric pressure. The volatile oil is a volatile cosmetic oil, which is liquid at room temperature, especially having a non-zero vapor pressure, at room temperature and atmospheric pressure, in particular having a vapor pressure ranging from 0.13 Pa to 40,000 Pa ($10^{-3}$ to 300 mmHg), preferably ranging from 1.3 Pa to 13,000 Pa (0.01 to 100 mmHg) and preferably ranging from 1.3 Pa to 1,300 Pa (0.01 to 10 mmHg).

In addition, the volatile oil generally has a boiling point, measured at atmospheric pressure, ranging from 150° C. to 260° C. and preferably ranging from 170° C. to 250° C.

The composition according to the invention may comprise a hydrocarbon-based volatile oil chosen especially from hydrocarbon-based oils with a flash point ranging from 40° C. to 102° C., preferably ranging from 40° C. to 55° C. and preferably ranging from 40° C. to 50° C.

Hydrocarbon-based volatile oils that may be mentioned include hydrocarbon-based volatile oils containing from 8 to 16 carbon atoms and mixtures thereof, and especially $C_8$-$C_{16}$ branched alkanes, for instance $C_8$-$C_{16}$ isoalkanes (also known as isoparaffins), isododecane, isodecane, isohexadecane and, for example, the oils sold under the trade names Isopar or Permethyl, $C_8$-$C_{16}$ branched esters, for instance isohexyl neopentanoate, and mixtures thereof. Preferably, the hydrocarbon-based volatile oil is chosen from hydrocarbon-based volatile oils containing from 8 to 16 carbon atoms, and mixtures thereof, in particular from isododecane, isodecane and isohexadecane, and is especially isododecane.

Volatile silicone oils that may be mentioned include linear or cyclic silicones containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof.

The composition according to the invention may comprise at least one non-volatile oil. Non-volatile hydrocarbon-based oils that may be used include, but are not limited to, liquid paraffin (or petroleum jelly), squalane, hydrogenated polyisobutylene (parleam oil), perhydrosqualene, mink oil, turtle oil, soybean oil, sweet almond oil, beauty-leaf oil, palm oil, grapeseed oil, sesame seed oil, corn oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, especially of $C_{12}$-$C_{36}$, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl)succinate, diisostearyl malate, and glyceryl or diglyceryl triisostearate; behenic acid, oleic acid, linoleic acid, linolenic acid or isostearic acid; higher fatty alcohols, especially of $C_{16}$-$C_{22}$, such as cetanol, oleyl alcohol, linoleyl alcohol, linolenyl alcohol, isostearyl alcohol or octyldodecanol; and mixtures thereof.

Suitable non-volatile silicone oils which may be used include, but are not limited to, polydimethylsiloxanes (PDMSs), that are optionally phenylated, such as phenyltrimethicones, phenyltrimethyl-siloxydiphenylsiloxanes, diphenylmethyldimethyltrisiloxanes, diphenyldimethicones, phenyldimethicones and polymethylphenylsiloxanes, optionally substituted with aliphatic and/or aromatic groups, or optionally fluorinated; polysiloxanes modified with fatty acids, fatty alcohols or polyoxyalkylenes, fluorosilicones and perfluorosilicone oils, and mixtures thereof.

Additional silicone non volatile oils may include, but are not limited to, hydrocarbyl functional siloxanes. Hydrocarbyl functional siloxanes comprise a siloxy unit of the formula $R^*R^i_{a1}SiO_{(3-a1)/2}$ wherein $R^i$ is any monovalent hydrocarbon group, but typically is an alkyl, cycloalkyl, alkenyl, aralkyl, or an aryl group containing 1-20 carbon atoms, $R^*$ is a hydrocarbyl group having the formula —$R^{**}OCH_2CH_2OH$;

$R^{**}$ is a divalent hydrocarbon group containing 2 to 6 carbon atoms, $a_1$ is zero to 2.

Organopolysiloxanes are well known in the art and are often designated as comprising any number of M units ($R^i_3SiO_{0.5}$), D units ($R^i_2SiO$), T units ($R^iSiO_{1.5}$), or Q units ($SiO_2$) where $R^i$ is independently any monovalent hydrocarbon group. In the present invention, the organopolysiloxane has at least one hydrocarbyl substituent of the formula —$R^{**}OCH_2CH_2OH$, designated as $R^*$. The $R^{}$ group in the hydrocarbyl substituent is a divalent hydrocarbon group containing 2 to 6 carbon atoms. The $R^{}$ divalent hydrocarbon is represented by an ethylene, propylene, butylene, pentylene, or hexylene. Typically, the divalent hydrocarbon is a propylene group, —$CH_2CH_2CH_2$—.

The hydrocarbyl substituent is bonded to the organopolysiloxane via a Si—C bond. The hydrocarbyl substituent can be present in the organopolysiloxane via linkage to any organosiloxy unit, that is it may be present on any M, D, or T siloxy unit. In other words, the hydrocarbyl functional siloxy unit can be a M unit ($R^*R^i_2SiO_{0.5}$), a D unit ($R^*R^iSiO$), a T unit ($R^*SiO_{0.5}$), or a mixture of any of these. The hydrocarbyl functional organopolysiloxane can also contain any number of additional M, D, T, or Q siloxy units of the general formula ($R^i_3SiO_{0.5}$), ($R^i_2SiO$), ($R^iSiO_{1.5}$), or ($SiO_2$), providing that the organopolysiloxane has at least one siloxy unit with the $R^1$ present.

The weight average molecular weight ($M_W$) or number average molecular weight ($M_N$) of the hydrocarbyl functional organopolysiloxane can vary, and is not limiting. The hydrocarbyl functional organopolysiloxane can be either liquid or solid in form, but are generally liquids.

The amount of the hydrocarbyl functional groups present in the organopolysiloxanes of the present invention can vary, but typically ranges from 1 to 40 mass percent, alternatively from 5 to 30 mass percent, or alternatively from 10 to 20 mass percent of the total mass of the organopolysiloxane.

In one embodiment, the hydrocarbyl functional organopolysiloxane has a formula selected from the following group:

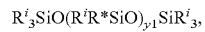

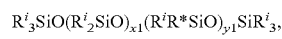

$R^*R^i_2SiO(R^i_2SiO)_{x1}(R^iR^*SiO)_{z1}SiR^i_2R^*$,

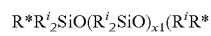

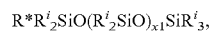

and cyclic siloxanes of the formula $-(Me_2SiO)_{m4}(MeR^*SiO)_{n4}$—

In these formulas, $R^i$ is an alkyl, cycloalkyl, alkenyl, aralkyl, or an aryl group containing 1-20 carbon atoms; $R^*$ is the hydrocarbyl group as defined above, $x_1$ is 1-500, $y_1$, is 1-40, $z_1$ is 1-40, $m_4$ is 1-6, $n_4$ is 1-6, and the sum of $m_4+n_4$ is 3-12.

In the alternate embodiment, the hydrocarbyl functional organopolysiloxane is a resin having the formula; $(SiO^2)_{c1}(R^1_3SiO_{3/2})_{d1}(R^{3*}_2SiO)_{e1}(R^{3*}_3SiO_{1/2})_{f1}\{O_{1/2}SiR^{3*}_2R^{4*}\}^{g1}$ where $R^{3*}$ is an alkyl group with 1-20 carbon atoms, a cycloalkyl group with 3-20 carbon atoms, an alkenyl group with 2-20 carbon atoms, an aralkyl group, or an aryl group; $R^{4*}$ is the same as $R^*$ above, i.e., one of the formulas (i) to (iv):

         (i)

         (ii)

         (iii)

         (iv);

and $g_1$ is 1-15,000. In such resins, $c_1$, $d_1$, $e_1$, and $f_1$ represent mole percents, such that $c_1<100$, $c_1+d_1>0$, and $c_1+d_1+e_1+f_1$ is 100. Organosiloxane resins of this type typically contain about 0.01-15 weight percent of silanol.

In a preferred embodiment, the hydrocarbyl functional organopolysiloxane has the formula $R^*Me_2SiO(Me_2SiO)_{x1}SiMe_2R^*$ where $R^*$ is —$(CH_2)_3OCH_2CH_2OH$ and $x_1$ is 1 to 100, alternatively 5 to 50, or alternatively 10 to 20.

The hydrocarbyl functional organopolysiloxanes of the present invention can be made by standard processes such as the hydrosilylation of organohydrogensiloxanes and olefinically substituted polyoxyalkylenes. The hydrosilylation reaction is typically performed in a low molecular weight volatile hydrocarbon solvent such as benzene, toluene, xylene, or isopropanol to aid in handling the reactants, to moderate an exothermic reaction or to promote the solubility of the reactants. Such processes are described, for example, in U.S. Pat. No. 2,283,218 patent which is incorporated herein by reference.

Other non volatile silicone oils may include phenyl substituted siloxanes:

The phenyl substituted organosiloxanes, in one embodiment, are defined by the following formula:

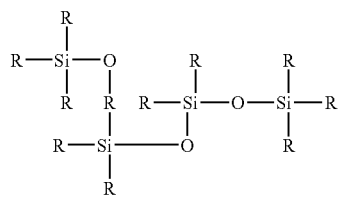

wherein R is a methyl or phenyl and wherein there are at least three phenyl groups in the organosiloxane. In certain embodiments, there are least four phenyl groups or five phenyl groups.

In another embodiment, the phenyl substituted organosiloxanes are defined by the following formula:

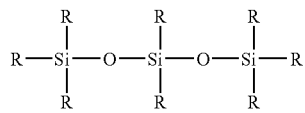

wherein R is a methyl or phenyl and where there are at least three phenyl groups in the organosiloxane. In certain embodiments, there are least four phenyl groups or five phenyl groups.

Mixtures of the above described phenyl substituted organosiloxanes may also be used. Suitable phenyl substituted organosiloxanes, for example, include mixtures having triphenyl substituted mixed with tetra and pentyl phenyl substituted organosiloxane. The phenyl substituted organosiloxanes may be purchased from a variety of commercial sources. Suitable sources include Dow Corning, for example, one preferred source is Dow Corning 555 Cosmetic Fluid having the INCI name trimethyl pentaphenyl trisiloxane, which is a mixture of about 60 to 90 parts trimethylpentaphenyltrisiloxane and from about 10 to 30 parts hexaphenyltetrasiloxane. In addition, Dow Corning 554 Cosmetic Fluid may also be used.

The oil may be present in an amount of from 0.1% to 95% by weight, preferably from 0.5% to 60% by weight and more preferably from 1% to 50% by weight, based on the weight of the composition.

Aqueous Phase:

The composition may employ an aqueous phase comprised of water, or a mixture of water and hydrophilic organic solvent(s), for instance alcohols and especially, linear or branched lower monoalcohols containing from 2 to 5 carbon atoms, for instance ethanol, isopropanol or n-propanol, and polyols, for instance glycerol, diglycerol, propylene glycol, sorbitol, pentylene glycol and polyethylene glycols, or alternatively hydrophilic $C_2$ ethers and $C_2$-$C_4$ aldehydes.

The water or the mixture of water and of hydrophilic organic solvents may be present in the composition according to the invention in an amount of from 0.1% to 95% by weight and preferably from 10% to 80% by weight, based on the weight of the composition.

Non-crosslinked Surfactant:

The composition according to the invention may also contain at least one non-crosslinked surfactant, so long as it is not chosen from polyglycerolated non-crosslinked silicone-based surfactants.

The non-crosslinked surfactant may be chosen from nonionic, anionic, cationic and amphoteric non-crosslinked surfactants.

The nonionic non-crosslinked surfactant may be chosen from:
a $C_8$-$C_{22}$ alkyl dimethicone copolyol, i.e. an oxypropylenated and/or oxyethylenated polymethyl($C_8$-$C_{22}$) alkyl dimethyl methyl siloxane.

The $C_8$-$C_{22}$ alkyl dimethicone copolyol is advantageously a compound of formula (I) below:

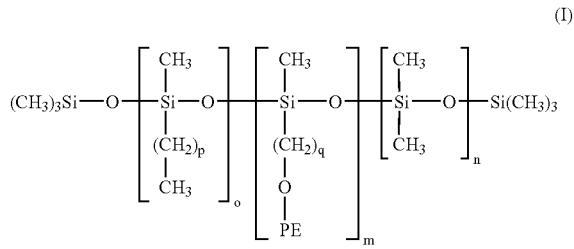

in which:
PE represents (—$C_2H_4O$)$_x$—($C_3H_6O$)$_y$—R, R being chosen from a hydrogen atom and an alkyl radical of 1 to 4 carbon atoms, x ranging from 0 to 100 and y ranging from 0 to 80, x and y not simultaneously being 0
m ranging from 1 to 40
n ranging from 10 to 200
o ranging from 1 to 100
p ranging from 7 to 21
q ranging from 0 to 4
and preferably:
R=H
m=1 to 10
n=10 to 100
o=1 to 30
p=15
q=3.

A $C_8$-$C_{22}$ alkyl dimethicone copolyol that may be mentioned is cetyl dimethicone copolyol, for instance the product sold under the name Abil EM-90 by the company Goldschmidt.

a dimethicone copolyol, i.e. an oxypropylenated and/or oxyethylenated polydimethyl methyl siloxane. It contains no alkyl groups with a chain length of more than 8 carbon atoms, especially $C_8$-$C_{22}$.

Dimethicone copolyols that may be used include those corresponding to formula (II) below:

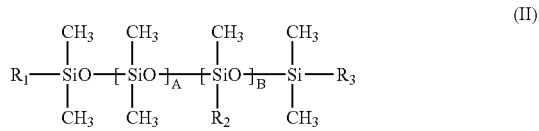

in which:

$R_1$, $R_2$ and $R_3$, independently of each other, represent a $C_1$-$C_6$ alkyl radical or a radical $-(CH_2)_x-(OCH_2CH_2)_y-(OCH_2CH_2)_z-OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50; on condition that A and B are not simultaneously equal to zero;

x is an integer ranging from 1 to 6;

y is an integer ranging from 1 to 30;

z is an integer ranging from 0 to 5.

According to one preferred embodiment of the invention, in the compound of formula (II), $R_1$=$R_3$=methyl radical, x is an integer ranging from 2 to 6 and y is an integer ranging from 4 to 30. $R_4$ is in particular a hydrogen.

Examples of compounds of formula (II) that may be mentioned include the compounds of formula (III):

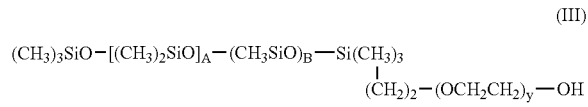

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

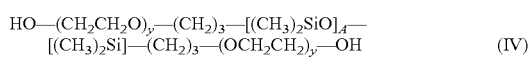

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016 and KF-6017 by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

Nonionic non-crosslinked surfactants that may also be mentioned include fatty acid esters of polyols, for-instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers.

Anionic non-crosslinked surfactants that may be mentioned include carboxylates (sodium 2-(2-hydroxyalkyloxy) acetate)), amino acid derivatives (N-acylglutamates, N-acylglycinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Amphoteric and zwitterionic noncrosslinked surfactants that may be used include betaines, N-alkylamidobetaines and derivatives thereof, glycine derivatives, sultaines, alkyl polyaminocarboxylates and alkylamphoacetates, and mixtures thereof.

Such surfactants are described especially in patent application WO02/056854, the entire content of which is hereby incorporated by reference.

Additional non-crosslinked surfactants work via steric stabilization. Examples of such surfactants include, but are not limited to, those obtained by grafting inulin, an essentially linear fructose based polymeric carbohydrate, with hydrophobic chains. The effectiveness of these surfactants is based on their role in stabilizing hydrophobic particles and oil droplets against flocculation and/or coalescence by a mechanism referred to as steric stabilization. Such surfactants are described in patents EP1086197 B1 and U.S. Pat. No. 6,534,647, the entire contents of which are hereby incorporated by reference. They are available as Inutec® surfactants from ORAFTI, Tienen, Belgium.

The non-crosslinked surfactant may be present in the composition according to the invention in an amount of from 0.1% to 10% by weight, preferably from 0.5% to 8% by weight, and more preferably from 1% to 7% by weight, based on the weight of the composition.

Dyestuffs:

The composition according to the invention may also contain at least one dyestuff.

The dyestuff may be chosen from pulverulent dyestuffs (especially pigments and nacres) and water-soluble dyestuffs.

The term "pigments" should be understood as meaning white or colored, mineral or organic particles of any form, which are insoluble in the physiological medium, and which are intended to color the composition.

The term "nacres" should be understood as meaning iridescent particles of any form, produced especially by certain mollusks in their shell, or else synthesized.

The pigments may be white or colored, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder.

Among the organic pigments that may be mentioned are carbon black, pigments of D & C type, and lakes based on cochineal carmine or on barium, strontium, calcium or aluminium.

Mention may also be made of pigments with an effect, such as particles comprising a natural or synthetic, organic or mineral substrate, for example glass, acrylic resins, polyester, polyurethane, polyethylene terephthalate, ceramics or aluminas, the said substrate being uncoated or coated with metallic substances, for instance aluminium, gold, silver, platinum, copper or bronze, or with metal oxides, for instance titanium dioxide, iron oxide or chromium oxide, and mixtures thereof.

The nacreous pigments may be chosen from white nacreous pigments such as mica coated with titanium or with bismuth oxychloride, colored nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride. Interference pigments, especially liquid-crystal or multilayer interference pigments, may also be used.

Coated Pigments:

Advantageously, the composition may comprise pigments treated with a hydrophobic agent. The hydrophobic treating agent may be chosen from silicones, for instance methicones, dimethicones, perfluoroalkylsilanes, perfluoroalkylsilazanes, triethoxy caprylylsilane, triethoxysilylethyl polydimethylsiloxyethyl hexyl dimethicone; fatty acids, for instance stearic acid; metal soaps, for instance aluminium dimyristate or the aluminium salt of hydrogenated tallow glutamate; perfluoroalkyl phosphates, polyhexafluoropropylene oxides, polyorganosiloxanes comprising perfluoroalkyl perfluoropolyether groups, silicone-grafted acrylic polymers (described especially in patent application JP05-339125 A, the entire content of which is hereby incorporated by reference); amino acids; N-acyl amino acids or salts thereof; lecithin, isopropyl triisostearyl titanate or isostearyl sebacate, and mixtures thereof.

The N-acyl amino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above especially denotes an alkyl group containing from 1 to 30 carbon atoms and preferably containing from 5 to 16 carbon atoms.

Hydrophobic-treated pigments are described especially in patent application EP1086683 A, the entire content of which is hereby incorporated by reference.

The water-soluble dyes are, for example, beetroot juice or methylene blue.

Other colorants may be encapsulated with water soluble materials or water insoluble materials. Products such as SUNSIL materials, encapsulated with silicone, are available from Sunjin Chemical Company. Additional dyestuffs coated with nylon or polymethyl methacrylate are also available from Sunjin Chemical Company.

The dyestuffs may be present in the composition in an amount of from 0.1% to 50% by weight, preferably from 0.5% to 30% by weight, and more preferably from 1% to 20% by weight, based on the weight of the composition.

Fillers:

The composition according to the invention may also comprise one or more fillers, especially in an amount of from 0.01% to 50% by weight and preferably from 0.01% to 30% by weight, based on the weight of the composition. The term "fillers" should be understood as meaning colorless or white, mineral or synthetic particles of any form, which are insoluble in the medium of the composition, irrespective of the temperature at which the composition is manufactured. These fillers serve especially to modify the rheology or texture of the composition.

The fillers may be mineral or organic, of any shape, platelet-shaped, spherical or oblong, irrespective of the crystallographic form (for example lamellar, cubic, hexagonal, orthorhombic, etc.). Mention may be made of talc, mica, silica, kaolin, polyamide (Nylon®) powders, (Orgasol® from Atochem), poly-β-alanine powder, polyethylene powder, tetrafluoroethylene polymer (Teflon®) powders, lauroyl lysine, starch, boron nitride, hollow polymer microspheres such as those of polyvinylidene chloride/acrylonitrile, for instance Expancel® (Nobel Industrie), or of acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrocarbonate, hydroxyapatite, hollow silica microspheres (Silica Beads® from Maprecos), glass or ceramic microcapsules, metal soaps derived from carboxylic organic acids containing from 8 to 22 carbon atoms and preferably from 12 to 18 carbon atoms, for example zinc stearate, magnesium stearate or lithium stearate, zinc laurate or magnesium myristate.

Additional fillers may include Glycospheres from KOBO, or

Softspheres from KOBO; Florabeads (jojoba esters+encapsulated material) from Floratech, Unispheres (cellulose and mannitol or lactose and Hydroxypropyl Methylcellulose+encapsulated material) from Induchem;

Lipopearls (Water and Gelatin and Cellulose gum+encapsulated material) from Lipo; Lipospheres (Water and Agar+encapsulated material) from Lipo.

The composition according to the invention may also contain ingredients commonly used in cosmetics, such as vitamins, thickeners, trace elements, softeners, sequestering agents, fragrances, acidifying or basifying agents, preserving agents, sunscreens, surfactants, antioxidants, agents for preventing hair loss, antidandruff agents and propellants, or mixtures thereof.

Needless to say, a person skilled in the art will take care to select this or these optional additional compound(s), and/or the amount thereof, such that the advantageous properties of the corresponding composition according to the invention are not, or are not substantially, adversely affected by the envisaged addition.

The composition according to the invention may especially be in the form of a suspension, a dispersion, a solution, a gel, an emulsion, especially an oil-in-water (O/W) or water-in-oil (W/O) emulsion, or a multiple emulsion (W/OW or polyol/O/W or O/W/O), in the form of a cream, a foam, a stick, a dispersion of vesicles, especially of ionic or nonionic lipids, a two-phase or multiphase lotion, a spray, a powder, a paste, especially a soft paste (especially a paste having a dynamic viscosity at 25° C. of about from 0.1 to 40 Pa.s at a shear rate of 200 s$^{-1}$, after 10 minutes of measurement in cone/plate geometry). The composition may be an anhydrous composition, i.e. a composition containing less than 2% by weight of water, or even less than 0.5% of water, and especially free of water, the water not being added during the preparation of the composition, but corresponding to the residual water provided by the mixed ingredients. The composition may be a leave-in composition.

A person skilled in the art will be able to select the appropriate galenical form, and also the method for preparing it, on the basis of his general knowledge, taking into account firstly the nature of the constituents used, especially their solubility in the support, and secondly the intended application of the composition.

The present invention is also directed to a process for treating a keratinous material involving contacting the keratinous material with the above-described composition. The precise amount of composition to be used will depend on the specific type of keratinous material being treated therewith and can easily be determined by those skilled in the art. The term "treating" includes, but is not limited to, caring for and making up keratinous materials. Examples thereof include, applying mascara to eyelashes, applying foundation to facial skin, applying lipstick onto lips, applying a sunscreen onto skin, and the like.

According to another aspect, the invention also relates to a cosmetic assembly comprising:
  i) a container delimiting at least one compartment, the said container being closed by a closing member; and
  ii) a composition placed inside the said compartment, the composition being in accordance with any one of the preceding claims.

The container may be in any adequate form. It may especially be in the form of a bottle, a tube, a jar, a case, a box, a sachet or a carton.

The closing member may be in the form of a removable stopper, a lid, a cap, a tear-off strip or a capsule, especially of the type comprising a body attached to the container and a cover cap articulated on the body. It may also be in the form of a member for selectively closing the container, especially a pump, a valve or a flap valve.

The container may be combined with an applicator, especially in the form of a brush comprising an arrangement of bristles maintained by a twisted wire. Such a twisted brush is described especially in patent U.S. Pat. No. 4,887,622, the entire content of which is hereby incorporated by reference. It may also be in the form of a comb comprising a plurality of application members, obtained especially by molding. Such combs are described, for example, in patent FR 2,796,529, the entire content of which is hereby incorporated by reference. The applicator may be in the form of a fine brush, as described, for example, in patent FR 2,722,380 the entire content of which is hereby incorporated by reference. The applicator may be in the form of a block of foam or of elastomer, a felt or a spatula. The applicator may be free (tuft or sponge) or securely fastened to a rod borne by the closing member, as described, for example, in patent U.S. Pat. No. 5,492,426 the entire content of which is hereby incorporated by reference. The applicator may be securely fastened to the container, as described, for example, in patent FR 2,761,959 the entire content of which is hereby incorporated by reference.

The product may be contained directly in the container, or indirectly. By way of example, the product may be arranged on an impregnated support, especially in the form of a wipe or a pad, and arranged (individually or in plurality) in a box or in a sachet. Such a support incorporating the product is described, for example, in patent application WO01/03538, the entire content of which is hereby incorporated by reference.

The closing member may be coupled to the container by screwing. Alternatively, the coupling between the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the said portion after the crossing of the bead or cord.

The container may be at least partially made of thermoplastic material. Examples of thermoplastic materials that may be mentioned include polypropylene or polyethylene.

Alternatively, the container is made of non-thermoplastic material, especially glass or metal (or alloy).

The container may have rigid walls or deformable walls, especially in the form of a tube or a tubular bottle.

The container may comprise means for distributing or facilitating the distribution of the composition. By way of example, the container may have deformable walls so as to allow the composition to exit in response to a positive pressure inside the container, this positive pressure being caused by elastic (or non-elastic) squeezing of the walls of the container. Alternatively, especially when the product is in the form of a stick, the product may be driven out by a piston mechanism. Still in the case of a stick, especially of makeup product (lipstick, foundation, etc.), the container may comprise a mechanism, especially a rack mechanism, a threaded-rod mechanism or a helical groove mechanism, and may be capable of moving a stick in the direction of the said aperture. Such a mechanism is described, for example, in patent FR 2,806,273 or in patent FR 2,775,566, the entire contents of which are hereby incorporated by reference. Such a mechanism for a liquid product is described in patent FR 2,727,609, the entire content of which is hereby incorporated by reference.

The container may consist of a carton with a base delimiting at least one housing containing the composition, and a lid, especially articulated on the base, and capable of at least partially covering the said base. Such a carton is described, for example, in patent application WO03/018423 or in patent FR 2,791,042 the entire contents of which are hereby incorporated by reference.

The container may be equipped with a drainer arranged in the region of the aperture of the container. Such a drainer makes it possible to wipe the applicator and possibly the rod to which it may be securely fastened. Such a drainer is described, for example, in patent FR 2,792,618 the entire content of which is hereby incorporated by reference.

The composition may be at atmospheric pressure inside the container (at room temperature) or pressurized, especially by means of a propellant gas (aerosol). In the latter case, the container is equipped with a valve (of the type used for aerosols).

The content of the patents or patent applications mentioned above are incorporated by reference into the present patent application.

The invention is illustrated in greater detail by the examples described below.

The amounts are expressed as percentages by weight.

EXAMPLE 1

A foundation having the following composition is prepared:

| EMULSION composition | |
|---|---|
| Cyclopentasiloxane | 5.00 |
| Dimethicone 10 cst (Fluid DC 200 10 cst from Dow Corning) | 9.00 |

-continued

| EMULSION composition | |
|---|---|
| 2-ethylhexyl methoxycinnamate (Parsol MCX from Roche Vitamins) | 1.00 |
| Isononyl isononanoate | 3.00 |
| C9-C15 Perfluoroalcohol phosphate and acrylates/dimethicone copolymer treated pigments* | 10.00 |
| PEG-10 Dimethicone/vinyl dimethicone crosspolymer (and) dimethicone (KSG-210 from Shin Etsu) | 5.00 |
| Dimethicone/polyglycerin-3 crosspolymer & dimethicone (KSG-710 from Shin Etsu) | 5.00 |
| Water | 50.50 |
| Butylene glycol | 9.00 |
| Preservative | 1.50 |
| Sodium chloride | 1.00 |
| TOTAL = | 100.00 |

*FSA-52 TiO$_2$ CR-50, FSA-52 Black BL-100, FSA-52 Red R-516L, FSA-52 Yellow LLXLO from KOBO This W/O emulsion with a high water content is smooth, silky and stable.

EXAMPLE 2

A foundation having the following composition is prepared:

| ANHYDROUS composition | |
|---|---|
| Neopentyl glycol dioctanoate | 15.00 |
| Isotridecyl isononanoate | 15.00 |
| Dimethicone 10 cst (Fluid DC 200 10 cst from Dow Corning) | 25.00 |
| Mica | 8.00 |
| Vinyl dimethicone/methicone silsesquioxane crosspolymer (KSP 100 from Shin Etsu) | 10.00 |
| Lauryl dimethicone/polyglycerin-3 crosspolymer & triethylhexanoin (KSG-830 from Shin Etsu) | 10.00 |
| Glycerol | 5.00 |
| Butylene glycol | 5.00 |
| C9-C15 Perfluoroalcohol phosphate and acrylates/dimethicone copolymer treated pigments* | 6.00 |
| Acrylates dimethicone copolymer (and) cyclopentasiloxane (KP545 from Shin Etsu) | 1.00 |
| TOTAL = | 100.00 |

*see Example 1

This non aqueous emulsion provides long wear and afterfeel with moisturizing properties. It does not feel heavy and greasy.

EXAMPLE 3

A foundation having the following composition is prepared:

| EMULSION composition | |
|---|---|
| Synthetic wax (Performa V 103 polymer from New Phase Technologies) | 2.00 |
| Ceresin | 6.50 |
| Cyclopentasiloxane | 2.00 |
| Dimethicone 10 cst (Fluid DC 200 10 cst from Dow Corning) | 10.00 |

-continued

| EMULSION composition | |
|---|---|
| Isononyl isononanoate | 13.50 |
| C9-C15 Perfluoroalcohol phosphate and acrylates/dimethicone copolymer treated pigments* | 12.80 |
| Cetyl dimethicone copolyol (Abil EM 90 from Goldschmit) | 1.50 |
| Polyglyceryl-4 isostearate | 0.50 |
| Dimethicone/polyglycerin-3 crosspolymer & dimethicone (KSG-710 from Shin Etsu) | 7.00 |
| Water | 36.00 |
| Butylene glycol | 7.00 |
| Preservative | 1.00 |
| Sodium citrate | 0.20 |
| TOTAL = | 100.00 |

*see Example 1

This solid W/O emulsion provides a moist and fresh feel upon application and provides a natural look.

EXAMPLE 4

A foundation having the following composition is prepared:

| EMULSION composition | |
|---|---|
| Disteardimonium hectorite | 0.50 |
| Cyclopentasiloxane | 10.00 |
| Dimethicone 10 cst (Fluid DC 200 10 cst from Dow Corning) | 14.00 |
| Glyceryl tri(12-hydroxystearate) (Thixcin R from Elementis) | 0.20 |
| Octyl palmitate | 9.00 |
| C9-C15 Perfluoroalcohol phosphate and acrylates/dimethicone copolymer treated pigments* | 10.00 |
| Nylon-66 fibers (FIBERLON 931-D1-S from LCW) | 2.00 |
| PEG-15 Lauryl dimethicone crosspolymer (and) triethylhexanoin (KSG-330 from Shin Etsu) | 3.00 |
| Dimethicone/polyglycerin-3 crosspolymer & dimethicone (KSG-710 from Shin Etsu) | 6.00 |
| Water | 33.80 |
| Butylene glycol | 9.00 |
| Preservative | 1.50 |
| Sodium chloride | 1.00 |
| TOTAL = | 100.00 |

*see Example 1

This liquid W/O emulsion provides a spongy, slippery application with a soft focus end look.

What is claimed is:

1. A composition comprising:
    a) at least one cosmetically acceptable medium;
    b) at least one polyglycerolated silicone elastomer;
    c) at least one ingredient chosen from at least one emulsifying elastomer different from the polyglycerolated silicone elastomer, at least one film forming polymer, at least one water soluble moisturizer, at least one coated pigment, at least one structuring agent, at least one photoprotective system capable of screening out UV radiation, at least one non-emulsifying spherical silicone elastomer, at least one fiber, at least one non-crosslinked surfactant, with the proviso that the non-crosslinked surfactant is not chosen from polyglycerolated non-crosslinked silicone surfactants, at least one hydrocarbyl-functional siloxane, at least one low molecular weight phenyl-substituted siloxane and at least one cosmetically-suitable active ingredient.

2. The composition of claim 1 wherein c) is at least one emulsifying elastomer different from b).

3. The composition of claim 1 wherein c) is at least one film forming polymer.

4. The composition of claim 1 wherein c) is at least one water soluble moisturizer.

5. The composition of claim 1 wherein c) is at least one coated pigment.

6. The composition of claim 1 wherein c) is at least one structuring agent.

7. The composition of claim 1 wherein c) is at least one photoprotective system capable of screening out UV radiation.

8. The composition of claim 1 wherein c) is at least one non-emulsifying spherical silicone elastomer.

9. The composition of claim 1 wherein c) is at least one fiber.

10. The composition of claim 1 wherein c) is at least one non-crosslinked surfactant, with the proviso that the non-crosslinked surfactant is not chosen from polyglycerolated non-crosslinked silicone surfactants.

11. The composition of claim 1 wherein c) is at least one hydrocarbyl modified siloxane.

12. The composition of claim 1 wherein c) is at least one low molecular weight phenyl-substituted siloxane.

13. The composition of claim 1 wherein c) is at least one cosmetically-suitable active ingredient.

14. A method for treating a keratinous material comprising contacting the keratinous material with a composition containing:
   a) at least one cosmetically acceptable medium;
   b) at least one polyglycerolated silicone elastomer;
   c) at least one ingredient chosen from at least one emulsifying elastomer different from the polyglycerolated silicone elastomer, at least one film forming polymer, at least one water soluble moisturizer, at least one coated pigment, at least one structuring agent, at least one photoprotective system capable of screening out UV radiation, at least one non-emulsifying spherical silicone elastomer, at least one fiber, at least one non-crosslinked surfactant, with the proviso that the non-crosslinked surfactant is not chosen from polyglycerolated non-crosslinked silicone surfactants, at least one hydrocarbyl-functional siloxane, at least one low molecular weight phenyl-substituted siloxane and at least one cosmetically-suitable active ingredient.

15. The method of claim 14 wherein c) is at least one emulsifying elastomer different from b).

16. The method of claim 14 wherein c) is at least one film-forming polymer.

17. The method of claim 14 wherein c) is at least one water soluble moisturizer.

18. The method of claim 14 wherein c) is at least one coated pigment.

19. The method of claim 14 wherein c) is at least one structuring agent.

20. The method of claim 14 wherein c) is at least one photoprotective system capable of screening out UV radiation.

21. The method of claim 14 wherein c) is at least one non-emulsifying spherical silicone elastomer.

22. The method of claim 14 wherein c) is at least one fiber.

23. The method of claim 14 wherein c) is at least one non-crosslinked surfactant, with the proviso that the non-crosslinked surfactant is not chosen from polyglycerolated non-crosslinked silicone surfactants.

24. The method of claim 14 wherein c) is at least one hydrocarbyl-functional siloxane.

25. The method of claim 14 wherein c) is at least one low molecular weight phenyl-substituted siloxane.

26. The method of claim 14 wherein c) is at least one cosmetically-suitable active ingredient.

* * * * *